(12) United States Patent
Ginggen et al.

(10) Patent No.: US 10,953,143 B2
(45) Date of Patent: Mar. 23, 2021

(54) METHODS AND DEVICES FOR MANIPULATING SUBDERMAL FAT

(71) Applicant: Cytrellis Biosystems, Inc., Woburn, MA (US)

(72) Inventors: Alec Ginggen, Medford, MA (US); Douglas Levinson, Sherborn, MA (US); David Stone, Acton, MA (US)

(73) Assignee: Cytrellis Biosystems, Inc., Woburn, MA (US)

( * ) Notice: Subject to any disclaimer, the term of this patent is extended or adjusted under 35 U.S.C. 154(b) by 859 days.

(21) Appl. No.: 15/106,036

(22) PCT Filed: Dec. 19, 2014

(86) PCT No.: PCT/US2014/071443
§ 371 (c)(1),
(2) Date: Jun. 17, 2016

(87) PCT Pub. No.: WO2015/095675
PCT Pub. Date: Jun. 25, 2015

(65) Prior Publication Data
US 2016/0317721 A1 Nov. 3, 2016

Related U.S. Application Data

(60) Provisional application No. 61/918,271, filed on Dec. 19, 2013.

(51) Int. Cl.
*A61M 1/00* (2006.01)
*A61B 17/3205* (2006.01)
*A61B 17/00* (2006.01)

(52) U.S. Cl.
CPC .......... *A61M 1/008* (2013.01); *A61M 1/0082* (2014.02); *A61B 17/32053* (2013.01);
(Continued)

(58) Field of Classification Search
CPC ............... A61M 1/008; A61M 1/0082; A61M 2202/08; A61B 17/32053; A61B 2017/00792
See application file for complete search history.

(56) References Cited

U.S. PATENT DOCUMENTS

| 2,426,535 A | 8/1947 | Turkel |
| 2,496,111 A | 1/1950 | Turkel |

(Continued)

FOREIGN PATENT DOCUMENTS

| AU | 2012 211 122 B2 | 7/2016 |
| CA | 1275215 C | 10/1990 |

(Continued)

OTHER PUBLICATIONS

Alsberg, E. et al., Engineering growing tissues, PNAS, 99(19):12025-12030 (2002).

(Continued)

*Primary Examiner* — Kai H Weng
(74) *Attorney, Agent, or Firm* — Choate, Hall & Stewart LLP; Brenda Herschbach Jarrell; Alexander D. Angst (57) ABSTRACT

The present invention features methods of manipulating subdermal fat in a treatment area. Such methods include inserting a needle (e.g., a micro-coring needle) through the dermis to the subdermal fat layer in order to excise a portion of tissue from the treatment area. These insertions result in a portion of the dermis and a portion of subdermal fat to enter into the needle. Removal of the needle results in excision of the portion of dermis and subdermal fat that entered into the needle.

24 Claims, 4 Drawing Sheets

(52) U.S. Cl.
CPC .............. *A61B 2017/00792* (2013.01); *A61M 2202/08* (2013.01)

(56) References Cited

U.S. PATENT DOCUMENTS

| | | | |
|---|---|---|---|
| 2,881,763 A | 4/1959 | Robbins | |
| 3,001,522 A | 9/1961 | Silverman | |
| 3,086,530 A | 4/1963 | Groom | |
| 3,214,869 A | 11/1965 | Stryker | |
| 3,598,108 A | 8/1971 | Jamshidi et al. | |
| 3,640,279 A | 2/1972 | Brown et al. | |
| 3,683,892 A | 8/1972 | Harris | |
| 3,788,320 A | 1/1974 | Dye | |
| 3,929,123 A | 12/1975 | Jamshidi | |
| 4,108,096 A | 8/1978 | Ciecior | |
| 4,159,659 A | 7/1979 | Nightingale | |
| 4,403,617 A | 9/1983 | Tretinyak | |
| 4,458,678 A | 7/1984 | Yannas et al. | |
| 4,476,864 A | 10/1984 | Tezel | |
| 4,604,346 A | 8/1986 | Bell et al. | |
| 4,640,296 A | 2/1987 | Schnepp-Pesch et al. | |
| 4,649,918 A | 3/1987 | Pegg et al. | |
| D297,375 S | 8/1988 | Liu | |
| 4,815,462 A | 3/1989 | Clark | |
| 4,865,026 A | 9/1989 | Barrett | |
| 4,903,709 A | 2/1990 | Skinner | |
| D323,034 S | 1/1992 | Reinstein | |
| 5,152,763 A | 10/1992 | Johnson | |
| D338,070 S | 8/1993 | Lam | |
| 5,242,453 A | 9/1993 | Gubich | |
| D342,138 S | 12/1993 | Wollman et al. | |
| 5,269,316 A | 12/1993 | Spitalny | |
| 5,306,490 A | 4/1994 | Barley, Jr. | |
| 5,324,305 A | 6/1994 | Kanner | |
| 5,331,972 A | 7/1994 | Wadhwani et al. | |
| 5,415,182 A | 5/1995 | Chin et al. | |
| 5,419,761 A | 5/1995 | Narayanan et al. | |
| 5,439,475 A | 8/1995 | Bennett | |
| 5,458,112 A | 10/1995 | Weaver | |
| D377,404 S | 1/1997 | Izumi | |
| 5,593,381 A | 1/1997 | Tannenbaum et al. | |
| 5,611,810 A | 3/1997 | Arnold et al. | |
| 5,615,690 A | 4/1997 | Giurtino et al. | |
| 5,639,654 A | 6/1997 | Bernard et al. | |
| D388,543 S | 12/1997 | Eguchi et al. | |
| 5,713,375 A | 2/1998 | McAllister | |
| 5,749,895 A | 5/1998 | Sawyer et al. | |
| 5,792,169 A | 8/1998 | Markman | |
| 5,810,857 A | 9/1998 | Mackool | |
| 5,827,297 A | 10/1998 | Boudjema | |
| 5,868,744 A | 2/1999 | Willmen | |
| 5,879,326 A | 3/1999 | Godshall et al. | |
| 5,885,211 A | 3/1999 | Eppstein et al. | |
| 5,885,226 A | 3/1999 | Rubinstein et al. | |
| 5,902,319 A | 5/1999 | Daley | |
| 5,922,000 A | 7/1999 | Chodorow | |
| 5,925,002 A | 7/1999 | Wollman | |
| 5,928,162 A | 7/1999 | Giurtino et al. | |
| 5,931,855 A | 8/1999 | Buncke | |
| 5,989,273 A | 11/1999 | Arnold | |
| 6,022,324 A | 2/2000 | Skinner | |
| D425,241 S | 5/2000 | Nishizawa et al. | |
| 6,059,807 A | 5/2000 | Boudjema | |
| 6,063,094 A | 5/2000 | Rosenberg | |
| 6,178,346 B1 | 1/2001 | Amundson et al. | |
| 6,197,039 B1 | 3/2001 | Ashraf | |
| 6,211,598 B1 | 4/2001 | Dhuler et al. | |
| 6,241,687 B1 | 6/2001 | Voegele et al. | |
| 6,241,739 B1 | 6/2001 | Waldron | |
| 6,251,097 B1 | 6/2001 | Kline et al. | |
| 6,264,618 B1 | 7/2001 | Landi et al. | |
| 6,342,213 B1 | 1/2002 | Barley et al. | |
| D457,265 S | 5/2002 | Gebhard | |
| D458,710 S | 6/2002 | Altamore et al. | |
| 6,419,641 B1 | 7/2002 | Mark et al. | |
| 6,432,098 B1 | 8/2002 | Kline et al. | |
| 6,440,086 B1 | 8/2002 | Hohenberg | |
| 6,461,369 B1 | 10/2002 | Kim | |
| 6,537,264 B1 | 3/2003 | Cormier et al. | |
| 6,562,037 B2 | 5/2003 | Paton et al. | |
| 6,669,618 B2 | 12/2003 | Reising et al. | |
| 6,669,694 B2 | 12/2003 | Shadduck | |
| 6,733,496 B2 | 5/2004 | Sharkey et al. | |
| 6,733,498 B2 | 5/2004 | Paton et al. | |
| D500,391 S | 12/2004 | Nielsen et al. | |
| 6,881,203 B2 | 4/2005 | Delmore et al. | |
| 6,887,250 B1 | 5/2005 | Dority et al. | |
| 6,893,388 B2 | 5/2005 | Reising et al. | |
| 6,936,039 B2 | 8/2005 | Kline et al. | |
| D509,301 S | 9/2005 | Talbot et al. | |
| 6,997,923 B2 | 2/2006 | Anderson et al. | |
| 7,073,510 B2 | 7/2006 | Redmond et al. | |
| 7,131,951 B2 | 11/2006 | Angel | |
| D538,430 S | 3/2007 | Ohta | |
| 7,618,429 B2 | 11/2009 | Mulholland | |
| 7,651,507 B2 | 1/2010 | Mishra et al. | |
| 7,658,728 B2 | 2/2010 | Yuzhakov | |
| 7,926,401 B2 | 4/2011 | Mishra et al. | |
| 8,128,639 B2 | 3/2012 | Tippett | |
| 8,209,006 B2 | 6/2012 | Smith et al. | |
| 8,226,664 B2 | 7/2012 | Drews et al. | |
| 8,246,611 B2 | 8/2012 | Paithankar et al. | |
| 8,435,791 B2 | 5/2013 | Galun et al. | |
| 8,480,592 B2 | 7/2013 | Chudzik et al. | |
| 8,696,686 B2 | 4/2014 | Drews et al. | |
| 8,900,181 B2 | 12/2014 | Knowlton | |
| 9,017,343 B2 | 4/2015 | Westerling, Jr. et al. | |
| 9,060,803 B2 | 6/2015 | Anderson et al. | |
| 9,084,465 B2 | 7/2015 | Oostman, Jr. et al. | |
| 9,119,945 B2 | 9/2015 | Simons et al. | |
| 9,439,673 B2 | 9/2016 | Austen | |
| 9,561,051 B2 | 2/2017 | Austen et al. | |
| D797,286 S | 9/2017 | Ginggen et al. | |
| 10,251,792 B2 | 4/2019 | Levinson et al. | |
| 10,543,127 B2 | 1/2020 | Levinson et al. | |
| 10,555,754 B2 | 2/2020 | Ginggen et al. | |
| 2001/0018572 A1 | 8/2001 | Kinsey et al. | |
| 2002/0022854 A1 | 2/2002 | Irion et al. | |
| 2002/0022861 A1 | 2/2002 | Jacobs et al. | |
| 2002/0045859 A1 | 4/2002 | Gartstein et al. | |
| 2002/0103500 A1 | 8/2002 | Gildenberg | |
| 2002/0120260 A1 | 8/2002 | Morris et al. | |
| 2002/0169431 A1 | 11/2002 | Kline et al. | |
| 2002/0183688 A1 | 12/2002 | Lastovich et al. | |
| 2002/0187556 A1 | 12/2002 | Shartle et al. | |
| 2002/0188280 A1 | 12/2002 | Nguyen et al. | |
| 2003/0023196 A1 | 1/2003 | Liguori | |
| 2003/0083607 A1 | 5/2003 | Bobo, Jr. | |
| 2003/0088220 A1 | 5/2003 | Molander et al. | |
| 2003/0119641 A1 | 6/2003 | Reising | |
| 2003/0135161 A1 | 7/2003 | Fleming et al. | |
| 2003/0144656 A1 | 7/2003 | Ocel et al. | |
| 2003/0158521 A1 | 8/2003 | Ameri | |
| 2003/0158566 A1* | 8/2003 | Brett | A61B 17/3403 606/167 |
| 2003/0163160 A1 | 8/2003 | O'Malley et al. | |
| 2003/0181936 A1 | 9/2003 | Trautman et al. | |
| 2003/0195625 A1 | 10/2003 | Garcia Castro et al. | |
| 2003/0199811 A1 | 10/2003 | Sage et al. | |
| 2003/0212415 A1 | 11/2003 | Karasiuk | |
| 2003/0233082 A1 | 12/2003 | Kline et al. | |
| 2004/0002723 A1 | 1/2004 | Ball | |
| 2004/0010268 A1 | 1/2004 | Gabehart | |
| 2004/0015139 A1 | 1/2004 | La Bianco et al. | |
| 2004/0019297 A1 | 1/2004 | Angel | |
| 2004/0023771 A1 | 2/2004 | Reising et al. | |
| 2004/0054410 A1 | 3/2004 | Barrows | |
| 2004/0073195 A1 | 4/2004 | Cucin | |
| 2004/0087992 A1 | 5/2004 | Gartstein et al. | |
| 2004/0122471 A1 | 6/2004 | Toby et al. | |
| 2004/0138680 A1 | 7/2004 | Twitchell et al. | |
| 2004/0162566 A1 | 8/2004 | Carson et al. | |
| 2004/0175690 A1 | 9/2004 | Mishra et al. | |
| 2004/0220589 A1 | 11/2004 | Feller | |

(56) References Cited

U.S. PATENT DOCUMENTS

| | | |
|---|---|---|
| 2005/0049582 A1 | 3/2005 | DeBenedictis et al. |
| 2005/0090765 A1 | 4/2005 | Fisher |
| 2005/0130821 A1 | 6/2005 | Reising et al. |
| 2005/0165329 A1 | 7/2005 | Taylor et al. |
| 2005/0171480 A1 | 8/2005 | Mukerjee et al. |
| 2005/0203575 A1 | 9/2005 | Carson et al. |
| 2005/0209567 A1 | 9/2005 | Sibbitt |
| 2005/0215921 A1 | 9/2005 | Hibner et al. |
| 2005/0215970 A1 | 9/2005 | Kline et al. |
| 2005/0215971 A1 | 9/2005 | Roe et al. |
| 2005/0226856 A1 | 10/2005 | Ahlfors |
| 2005/0234419 A1 | 10/2005 | Kline et al. |
| 2005/0245952 A1 | 11/2005 | Feller |
| 2005/0283141 A1 | 12/2005 | Giovannoli |
| 2006/0047234 A1 | 3/2006 | Glucksman et al. |
| 2006/0064031 A1 | 3/2006 | Miller |
| 2006/0116605 A1 | 6/2006 | Nakao |
| 2006/0155266 A1 | 7/2006 | Manstein et al. |
| 2006/0161179 A1 | 7/2006 | Kachenmeister |
| 2006/0184153 A1 | 8/2006 | Mark et al. |
| 2006/0193819 A1 | 8/2006 | Lu et al. |
| 2006/0216781 A1 | 9/2006 | Gebing |
| 2006/0259006 A1 | 11/2006 | McKay et al. |
| 2006/0264926 A1 | 11/2006 | Kochamba |
| 2006/0271070 A1 | 11/2006 | Eriksson et al. |
| 2006/0276806 A1 | 12/2006 | Martinez Zunino |
| 2007/0010810 A1 | 1/2007 | Kochamba |
| 2007/0038181 A1 | 2/2007 | Melamud et al. |
| 2007/0038236 A1 | 2/2007 | Cohen |
| 2007/0060888 A1 | 3/2007 | Goff et al. |
| 2007/0073217 A1 | 3/2007 | James |
| 2007/0073327 A1 | 3/2007 | Giovannoli |
| 2007/0078359 A1 | 4/2007 | Luloh et al. |
| 2007/0078466 A1 | 4/2007 | Bodduluri et al. |
| 2007/0078473 A1 | 4/2007 | Bodduluri et al. |
| 2007/0106306 A1 | 5/2007 | Bodduluri et al. |
| 2007/0142722 A1 | 6/2007 | Chang |
| 2007/0142744 A1 | 6/2007 | Provencher |
| 2007/0142885 A1 | 6/2007 | Hantash et al. |
| 2007/0149991 A1 | 6/2007 | Mulholland |
| 2007/0156161 A1 | 7/2007 | Weadock et al. |
| 2007/0167958 A1 | 7/2007 | Sulamanidze et al. |
| 2007/0179455 A1 | 8/2007 | Geliebter et al. |
| 2007/0183938 A1 | 8/2007 | Booker |
| 2007/0198000 A1 | 8/2007 | Miyamoto et al. |
| 2007/0213634 A1 | 9/2007 | Teague |
| 2007/0239236 A1 | 10/2007 | Manstein |
| 2007/0239260 A1 | 10/2007 | Palanker et al. |
| 2007/0249960 A1 | 10/2007 | Williamson |
| 2007/0270710 A1 | 11/2007 | Frass et al. |
| 2008/0009802 A1 | 1/2008 | Lambino et al. |
| 2008/0009901 A1 | 1/2008 | Redmond et al. |
| 2008/0033334 A1 | 2/2008 | Gurtner et al. |
| 2008/0045858 A1 | 2/2008 | Tessitore et al. |
| 2008/0045861 A1 | 2/2008 | Miller et al. |
| 2008/0132979 A1 | 6/2008 | Gerber |
| 2008/0146982 A1 | 6/2008 | Rastegar et al. |
| 2008/0183167 A1 | 7/2008 | Britva et al. |
| 2008/0208146 A1 | 8/2008 | Brandwein et al. |
| 2008/0221548 A1 | 9/2008 | Danenberg et al. |
| 2008/0234602 A1 | 9/2008 | Oostman et al. |
| 2008/0234699 A1 | 9/2008 | Oostman, Jr. et al. |
| 2008/0269735 A1 | 10/2008 | Vila Echague et al. |
| 2008/0275378 A1 | 11/2008 | Herndon |
| 2008/0300507 A1 | 12/2008 | Figueredo et al. |
| 2008/0306471 A1 | 12/2008 | Altshuler et al. |
| 2008/0312648 A1 | 12/2008 | Peterson |
| 2009/0030340 A1 | 1/2009 | Mc Clellan |
| 2009/0048557 A1 | 2/2009 | Yeshurun et al. |
| 2009/0088720 A1 | 4/2009 | Oostman, Jr. |
| 2009/0093864 A1 | 4/2009 | Anderson |
| 2009/0146068 A1 | 6/2009 | Agarwal |
| 2009/0163877 A1 | 6/2009 | Christoffersen et al. |
| 2009/0198336 A1 | 8/2009 | Qiao et al. |
| 2009/0227895 A1 | 9/2009 | Goldenberg |
| 2009/0312749 A1 | 12/2009 | Pini et al. |
| 2010/0023003 A1 | 1/2010 | Mulholland |
| 2010/0041938 A1 | 2/2010 | Stoianovici et al. |
| 2010/0057100 A1 | 3/2010 | Zeevi |
| 2010/0082042 A1 | 4/2010 | Drews |
| 2010/0121307 A1 | 5/2010 | Lockard et al. |
| 2010/0145373 A1 | 6/2010 | Alon |
| 2010/0160822 A1 | 6/2010 | Parihar et al. |
| 2010/0185116 A1 | 7/2010 | Al-Mohizea |
| 2010/0330589 A1 | 12/2010 | Bahrami et al. |
| 2011/0009882 A1 | 1/2011 | Remsburg et al. |
| 2011/0028898 A1 | 2/2011 | Clark, III et al. |
| 2011/0040497 A1 | 2/2011 | Olesen |
| 2011/0046616 A1 | 2/2011 | Manstein |
| 2011/0092844 A1 | 4/2011 | Bargo et al. |
| 2011/0105949 A1 | 5/2011 | Wiksell |
| 2011/0152738 A1 | 6/2011 | Zepeda et al. |
| 2011/0166520 A1 | 7/2011 | Iwase et al. |
| 2011/0172745 A1 | 7/2011 | Na et al. |
| 2011/0245834 A1 | 10/2011 | Miklosovic |
| 2011/0251602 A1 | 10/2011 | Anderson et al. |
| 2011/0257588 A1 | 10/2011 | Knowlton |
| 2011/0270274 A1 | 11/2011 | Hull, Jr. |
| 2011/0282238 A1 | 11/2011 | Houser et al. |
| 2011/0313345 A1 | 12/2011 | Schafer |
| 2011/0313429 A1 | 12/2011 | Anderson et al. |
| 2012/0041430 A1 | 2/2012 | Anderson et al. |
| 2012/0065551 A1 | 3/2012 | Aviad et al. |
| 2012/0136387 A1 | 5/2012 | Redmond et al. |
| 2012/0158100 A1 | 6/2012 | Schomacker |
| 2012/0209283 A1 | 8/2012 | Zhu |
| 2012/0226214 A1 | 9/2012 | Gurtner et al. |
| 2012/0226268 A1 | 9/2012 | Liu et al. |
| 2012/0226306 A1 | 9/2012 | Jackson et al. |
| 2012/0245629 A1 | 9/2012 | Gross et al. |
| 2012/0253333 A1 | 10/2012 | Garden et al. |
| 2012/0259237 A1 | 10/2012 | Axelrod |
| 2012/0271320 A1 | 10/2012 | Hall et al. |
| 2013/0006168 A1 | 1/2013 | Del Vecchio |
| 2013/0041397 A1 | 2/2013 | Nishimura |
| 2013/0045171 A1 | 2/2013 | Utecht et al. |
| 2013/0110026 A1 | 5/2013 | Jackson et al. |
| 2013/0131635 A1* | 5/2013 | Rimsa ................ A61M 5/1452 604/506 |
| 2013/0204238 A1 | 8/2013 | Lederman et al. |
| 2014/0036523 A1 | 2/2014 | Thullier et al. |
| 2014/0039523 A1 | 2/2014 | Austen |
| 2014/0163582 A1 | 6/2014 | Austen et al. |
| 2014/0200484 A1 | 7/2014 | Austen et al. |
| 2014/0249547 A1 | 9/2014 | Boone, III |
| 2014/0277055 A1 | 9/2014 | Austen, Jr. |
| 2014/0296741 A1 | 10/2014 | Austen |
| 2014/0296796 A1 | 10/2014 | Lim |
| 2014/0303648 A1 | 10/2014 | Knowlton |
| 2014/0343481 A1 | 11/2014 | Ignon |
| 2015/0143713 A1 | 5/2015 | Cheng |
| 2015/0173991 A1 | 6/2015 | Anderson et al. |
| 2015/0238214 A1 | 8/2015 | Anderson et al. |
| 2015/0258319 A1 | 9/2015 | Simmers |
| 2015/0320990 A1 | 11/2015 | Burton et al. |
| 2015/0366719 A1 | 12/2015 | Levinson et al. |
| 2016/0082241 A1 | 3/2016 | Burton et al. |
| 2016/0095592 A1 | 4/2016 | Levinson et al. |
| 2016/0121091 A1 | 5/2016 | Burton et al. |
| 2016/0129198 A1 | 5/2016 | Bitar et al. |
| 2016/0136406 A1 | 5/2016 | Berry et al. |
| 2016/0192961 A1 | 7/2016 | Ginggen et al. |
| 2016/0367280 A1 | 12/2016 | Austen |
| 2017/0367729 A1 | 12/2017 | Ginggen et al. |
| 2018/0008500 A1 | 1/2018 | Anderson et al. |
| 2018/0021087 A1 | 1/2018 | Anderson et al. |
| 2018/0078278 A1 | 3/2018 | Levinson et al. |
| 2018/0185196 A1 | 7/2018 | Levinson et al. |
| 2018/0193054 A1 | 7/2018 | Austen |
| 2018/0206875 A1 | 7/2018 | Austen et al. |
| 2019/0099199 A1 | 4/2019 | Levinson et al. |
| 2019/0366067 A1 | 12/2019 | Ginggen et al. |
| 2020/0038051 A1 | 2/2020 | Austen |
| 2020/0121354 A1 | 4/2020 | Ginggen et al. |

(56) References Cited

U.S. PATENT DOCUMENTS

| | | |
|---|---|---|
| 2020/0188184 A1 | 6/2020 | Levinson et al. |
| 2020/0214766 A1 | 7/2020 | Anderson et al. |
| 2020/0246039 A1 | 8/2020 | Levinson et al. |

FOREIGN PATENT DOCUMENTS

| | | |
|---|---|---|
| CA | 2361777 A1 | 5/2002 |
| CN | 2126570 Y | 1/1993 |
| CN | 1115629 A | 1/1996 |
| CN | 201005966 Y | 1/2008 |
| CN | 101128156 A | 2/2008 |
| CN | 101208128 A | 6/2008 |
| CN | 101232858 A | 7/2008 |
| CN | 101277657 A | 10/2008 |
| CN | 101312692 A | 11/2008 |
| CN | 101347346 A | 1/2009 |
| CN | 101563113 A | 10/2009 |
| CN | 101670145 A | 3/2010 |
| CN | 102119006 A | 7/2011 |
| CN | 102143724 A | 8/2011 |
| CN | 102178616 A | 9/2011 |
| CN | 202113484 U | 1/2012 |
| CN | 103547226 A | 1/2014 |
| DE | 287651 A5 | 3/1991 |
| DE | 202004010659 U1 | 10/2004 |
| DE | 102007026973 A1 | 12/2008 |
| EP | 0027974 A1 | 5/1981 |
| EP | 1224949 A1 | 7/2002 |
| EP | 1278061 A1 | 1/2003 |
| EP | 1396230 A1 | 3/2004 |
| EP | 1618925 A1 | 1/2006 |
| EP | 2181732 A1 | 5/2010 |
| EP | 1278061 B1 | 2/2011 |
| EP | 2409727 A1 | 1/2012 |
| FR | 2846221 B1 | 7/2005 |
| JP | S57-163208 A | 10/1982 |
| JP | 2000-139929 A | 5/2000 |
| JP | 2001-187058 A | 7/2001 |
| JP | 2002-505605 A | 2/2002 |
| JP | 2003-515424 A | 5/2003 |
| JP | 2003-532480 A | 11/2003 |
| JP | 2004-503342 A | 2/2004 |
| JP | 2005-000642 A | 1/2005 |
| JP | 2005-87519 A | 4/2005 |
| JP | 2005-87520 A | 4/2005 |
| JP | 2005-103276 A | 4/2005 |
| JP | 2006-516201 A | 6/2006 |
| JP | 2006-517814 A | 8/2006 |
| JP | 2007-041267 A | 2/2007 |
| JP | 2007-100140 A | 4/2007 |
| JP | 2008-036393 A | 2/2008 |
| JP | 2008-528207 A | 7/2008 |
| JP | 2009-502413 A | 1/2009 |
| JP | 2009-507773 A | 2/2009 |
| JP | 2009-509671 A | 3/2009 |
| JP | 2009-172418 A | 8/2009 |
| JP | 2009-219858 A | 10/2009 |
| JP | 2009-545382 A | 12/2009 |
| JP | 2010-000210 A | 1/2010 |
| JP | 4431637 B2 | 3/2010 |
| JP | 2010-515469 A | 5/2010 |
| JP | 2010-524591 A | 7/2010 |
| JP | 2010-525887 A | 7/2010 |
| JP | 2011-516169 A | 5/2011 |
| JP | 2013-526300 A | 6/2013 |
| JP | 2014-506498 | 3/2014 |
| JP | 5944925 B2 | 7/2016 |
| KR | 2008-0030553 A | 4/2008 |
| KR | 2008-0049793 A | 6/2008 |
| KR | 2010-0135863 A | 12/2010 |
| KR | 2010-0135864 A | 12/2010 |
| RU | 1801391 C | 3/1993 |
| RU | 2119304 C1 | 9/1998 |
| RU | 2289332 C2 | 12/2006 |
| RU | 2308873 C2 | 10/2007 |
| RU | 2325859 C2 | 6/2008 |
| TW | 402497 B | 8/2000 |
| TW | 200841866 A | 11/2008 |
| WO | WO-93/22971 A1 | 11/1993 |
| WO | WO-1995/28896 A1 | 11/1995 |
| WO | WO-97/18758 A1 | 5/1997 |
| WO | WO-98/26719 A1 | 6/1998 |
| WO | WO-98/57587 A1 | 12/1998 |
| WO | WO-99/29243 A1 | 6/1999 |
| WO | WO-0141651 A2 | 6/2001 |
| WO | WO-01/85035 A1 | 11/2001 |
| WO | WO-02/05890 A2 | 1/2002 |
| WO | WO-02/096321 A1 | 12/2002 |
| WO | WO-2004/045671 A2 | 6/2004 |
| WO | WO-2004/107984 A1 | 12/2004 |
| WO | WO-2005/013830 A1 | 2/2005 |
| WO | WO-2005/072181 A2 | 8/2005 |
| WO | WO-2005/109799 A2 | 11/2005 |
| WO | WO-2006/081556 A2 | 8/2006 |
| WO | WO-2006/116281 A2 | 11/2006 |
| WO | WO-2006/118804 A1 | 11/2006 |
| WO | WO-2007/011788 A2 | 1/2007 |
| WO | WO-2007/015232 A1 | 2/2007 |
| WO | WO-2007/015247 A2 | 2/2007 |
| WO | WO-2007/024038 A1 | 3/2007 |
| WO | WO-2007/041267 A2 | 4/2007 |
| WO | WO-2007/066339 A1 | 6/2007 |
| WO | WO-2007/080596 A2 | 7/2007 |
| WO | WO-2007/106170 A2 | 9/2007 |
| WO | WO-2008/019051 A2 | 2/2008 |
| WO | WO-2008/033873 A2 | 3/2008 |
| WO | WO-2008/052189 A2 | 5/2008 |
| WO | WO-2008/131302 A2 | 10/2008 |
| WO | WO-2009/040493 A1 | 4/2009 |
| WO | WO-2009/072711 A2 | 6/2009 |
| WO | WO-2009/099988 A2 | 8/2009 |
| WO | WO-2009/137288 A2 | 11/2009 |
| WO | WO-2009/146053 A1 | 12/2009 |
| WO | WO-2009/146068 A1 | 12/2009 |
| WO | WO-2009/146072 A1 | 12/2009 |
| WO | WO-2010/027188 A2 | 3/2010 |
| WO | WO-2010/080014 A2 | 7/2010 |
| WO | WO-2010/095456 A1 | 8/2010 |
| WO | WO-2010/097790 A1 | 9/2010 |
| WO | WO-2011/006009 A1 | 1/2011 |
| WO | WO-2011/019859 A1 | 2/2011 |
| WO | WO-2011/075676 A2 | 6/2011 |
| WO | WO-2011/104875 A1 | 9/2011 |
| WO | WO-2011/123218 A1 | 10/2011 |
| WO | WO-2011/075676 A3 | 11/2011 |
| WO | WO-2011140497 A2 | 11/2011 |
| WO | WO-2012/052986 A2 | 4/2012 |
| WO | WO-2012/103483 A2 | 8/2012 |
| WO | WO-2012/103488 A1 | 8/2012 |
| WO | WO-2012/103492 A1 | 8/2012 |
| WO | WO-2012/119131 A1 | 9/2012 |
| WO | WO-2012/135828 A1 | 10/2012 |
| WO | WO-2013/013196 A1 | 1/2013 |
| WO | WO-2013/013199 A2 | 1/2013 |
| WO | WO-2013/104414 A1 | 7/2013 |
| WO | WO-2014/008470 A1 | 1/2014 |
| WO | WO-2014/008481 A1 | 1/2014 |
| WO | WO-2014/089488 A2 | 6/2014 |
| WO | WO-2014/130359 A1 | 8/2014 |
| WO | WO-2014/151104 A1 | 9/2014 |
| WO | WO-2014/179729 A1 | 11/2014 |
| WO | WO-2015/021434 A2 | 2/2015 |
| WO | WO-2015/051164 A2 | 4/2015 |
| WO | WO-2015/095675 A1 | 6/2015 |
| WO | WO-2015/126926 A1 | 8/2015 |
| WO | WO-2016/033584 A1 | 3/2016 |
| WO | WO-2016/033586 A1 | 3/2016 |
| WO | WO-2016/077759 A1 | 5/2016 |
| WO | WO-2016/127091 A1 | 8/2016 |
| WO | WO-2017/139773 A2 | 8/2017 |
| WO | WO-2017/172920 A1 | 10/2017 |
| WO | WO-2017/192723 A1 | 11/2017 |

(56) References Cited

FOREIGN PATENT DOCUMENTS

| WO | WO-2018/057630 A1 | 3/2018 |
|---|---|---|
| WO | WO-2018/057637 A1 | 3/2018 |
| WO | WO-2020/097244 A1 | 5/2020 |

OTHER PUBLICATIONS

Banzhaf, C. et al., Spatiotemporal Closure of Fractional Laser-Ablated Channels Imaged by Optical Coherence Tomography and Reflectance Confocal Microscopy, Lasers in Surgery and Medicine, 48:157-165 (2016).
Bedi, V. et al., The effects of pulse energy variations on the dimensions of microscopic thermal treatment zones in nonablative fractional resurfacinq, Lasers Surg Med, 39(2):145-55 (2007).
Cevc, Gregor, Drug delivery across the skin, Expert Opinion Investigational Drugs, 6(12):1887-937 (1997).
Chang, Te-Sheng, An updated review of tyrosinase inhibitors, Int J Mol Sci, 10(6):2440-2475 (2009).
International Search Report for International Patent Application No. PCT/US2012/022980 dated Aug. 9, 2012.
International Written Opinion for International Patent Application No. PCT/US2012/022980 dated Aug. 9, 2012.
Czech, Z. et al., Pressure-sensitive adhesives for medical applications, Wide Spectra of Quality Control, Akyar, 309-332 (2011).
de las Heras Alarcon et al., Stimuli responsive polymers for biomedical applications, Chem Soc Rev. 34(3):276-85 (2005).
Dini, G. et al., Grasping leather plies by Bernoulli grippers, CIRP Ann Manuf Technol. 58(1):21-4 (2009).
Dujardin, J. et al., In vivo assessment of skin electroporation using square wave pulses, J Control Release, 79(1-3):219-27 (2002).
Dunkin, C. et al., Scarring occurs at a critical depth of skin injury: precise measurement in a graduated dermal scratch in human volunteers, Plast Reconstr Surg, 119(6):1722-32 (2007).
European Patent Office, Supplementary European Search Report, Application No. EP13813955.5, dated Mar. 18, 2016.
European Search Report for European Application No. 12739664.6 dated May 20, 2014.
Extended European Search Report, Application No. 12814711.3, datd Feb. 11, 2015.
Fernandes, J. et al., Micro-mechanical fractional skin rejuvenation, Plast Reconstr Surg, 130(5S-1):28 (2012).
Fernandes, J. et al., Micro-mechanical fractional skin rejuvenation, Plast Reconstr Surg, 131(2):216-23 (2013).
Galaev., 'Smart' polymers in biotechnology and medicine, Russ Chem Rev. 64(5):471-489 (1995).
Hale, G. and Querry, M., Optical constants of water in the 200-nm to 200-microm wavelength region, Appl Opt, 12(3):555-63 (1973).
Han, H. et al., Combined, Minimally Invasive, Thread-based Facelift, Archives of Aesthetic Plastic Surgery, 20(3):160-164 (2014).
Huang, W.M. et al., Shape memory materials, Material Today, 13(7-8):54-61 (2010).
International Preliminary Report on Patentability for International Patent Application No. PCT/US2009/039125, dated Oct. 5, 2010 (6 pages).
International Preliminary Report on Patentability for International Patent Application No. PCT/US2012/022987, dated Jul. 30, 2013 (5 pages).
International Preliminary Report on Patentability for International Patent Application No. PCT/US2012/022993, dated Jul. 30, 2013 (5 pages).
International Preliminary Report on Patentability for International Patent Application No. PCT/US2012/047716, dated Nov. 4, 2014 (4 pages).
International Preliminary Report on Patentability for International Patent Application No. PCT/US2013/049445, dated Jan. 6, 2015 (4 pages).
International Preliminary Report on Patentability for International Patent Application No. PCT/US2014/036638, dated Nov. 3, 2015 (7 pages).
International Preliminary Report on Patentability for International Patent Application No. PCT/US2014/050426, dated Feb. 9, 2016 (8 pages).
International Search Report and Written Opinion for International Patent Application No. PCT/US2009/039125, dated Nov. 16, 2009 (9 pages).
International Search Report and Written Opinion for International Patent Application No. PCT/US2012/022987, dated Apr. 12, 2012 (6 pages).
International Search Report and Written Opinion for International Patent Application No. PCT/US2012/022993, dated May 17, 2012 (6 pages).
International Search Report and Written Opinion for International Patent Application No. PCT/US2012/047716, dated Oct. 25, 2012 (5 pages).
International Search Report and Written Opinion for International Patent Application No. PCT/US2013/049445, dated Oct. 18, 2013 (5 pages).
International Search Report and Written Opinion for International Patent Application No. PCT/US2014/016483, dated May 6, 2014 (9 pages).
International Search Report and Written Opinion for International Patent Application No. PCT/US2014/036638, dated Oct. 2, 2014 (10 pages).
International Search Report and Written Opinion for International Patent Application No. PCT/US2014/050426, dated Feb. 4, 2015 (11 pages).
International Search Report and Written Opinion for PCT/US2011/035613, dated May 6, 2011.
International Search Report and Written Opinion issued by the Korean Intellectual Property Office as International Searching Authority for International Application No. PCT/US2009/039114 dated Nov. 16, 2009 (10 pages).
International Search Report and Written Opinion under dated Oct. 18, 2013 in connection with PCT/US2013/049445.
International Search Report for International Patent Application No. PCT/US2012/047708.
International Search Report for PCT/US14/71443, 3 pages (dated Mar. 19, 2015).
International Search Report for PCT/US2015/060685, 3 pages (dated Feb. 2, 2016).
International Search Report for PCT/US2017/024752, 8 pages (dated Aug. 29, 2017).
International Search Report for PCT/US2017/052528 (Devices and Methods for Cosmetic Skin Resurfacing, filed Sep. 20, 2017), issued by ISA/US, 5 pages (dated Jan. 4, 2018).
International Search Report for PCT/US2017/052539 (Rapid Skin Treatment Using Microcoring, filed Sep. 20, 2017), issued by ISA/US, 7 pages (dated Nov. 22, 2017).
International Searching Report and Written Opinion issued by the Korean Intellectual Property Office as International Search Authority for International Application No. PCT/US2011 /035613 dated Jan. 12, 2012 (6 pages).
Kakasheva-Mazenkovska, L. et al., Variations of the histomorphological characteristics of human skin of different body regions in subjects of different age, Contributions, 32(2):119-28 (2011).
Konermann, W. et al., Ultrasonographically guided needle biopsy of benign and malignant soft tissue and bone tumors, J Ultrasound Med, 19(7):465-71 (2000).
Lemperle, G. et al., A Classification of Facial Wrinkles, Plastic and Reconstructive Surgery, 108(6):1735-1750 (2001).
Lien, T.K. and Davis, P.G.G., A novel gripper for limp materials based on lateral Coanda ejectors, CIRP Ann Manuf Technol, 57(1):33-6 (2008).
Majid, Imran, Microneedling therapy in atrophic facial scars: an objective assessment, J Cutan Aesthet Surg. 2(1):26-30 (2009).
Moore, J. et al., Modeling of the Plane Needle Cutting Edge Rake and Inclination Angles for Biopsy, Journal of Manufacturing Science and Engineering, 132:051005-1-051005-8 (2010).
Narins, R. et al., Validated Assessment Scales for the Lower Face, Dermatology Surgery, 38:333-342 (2012).
PCT International Preliminary Report on Patentability, PCT/US2014/036638, dated Nov. 3, 2015, 7 pages.

(56) References Cited

OTHER PUBLICATIONS

PCT International Preliminary Report on Patentability, PCT/US2014/050426, dated Feb. 9, 2016, 8 pages.
PCT International Search Report and Written Opinion, PCT/US2014/036638, dated Oct. 2, 2014, 10 pages.
PCT International Search Report and Written Opinion, PCT/US2014/050426, dated Feb. 4, 2015, 18 pages.
Pliquett, U. et al., A propagating heat wave model of skin electroporation, J Theor Biol, 251(2):195-201 (2008).
Prausnitz, M. et al., Electroporation of mammalian skin: a mechanism to enhance transdermal drug delivery, Proc Natl Acad Sci USA, 90(22):10504-8 (1993).
Salam, G. and Amin, J., The basic Z-plasty, Am Fam Physician, 67(11):2329-32 (2003).
Written Opinion for International Patent Application No. PCT/US2012/047708.
Written Opinion for PCT/US14/71443, 4 pages (dated Mar. 19, 2015).
Written Opinion for PCT/US2014/016483, 6 pages (dated May 6, 2014).
Written Opinion for PCT/US2015/060685, 4 pages (dated Feb. 2, 2016).
Written Opinion for PCT/US2017/024752, 11 pages (dated Aug. 29, 2017).
Written Opinion for PCT/US2017/052528 (Devices and Methods for Cosmetic Skin Resurfacing, filed Sep. 20, 2017), issued by ISA/US, 17 pages (dated Jan. 4, 2018).
Written Opinon for PCT/US2017/052539 (Rapid Skin Treatment Using Microcoring, filed Sep. 20, 2017), issued by ISA/US, 8 pages (dated Nov. 22, 2017).
Zhu, J. et al., the Efficacy and Safety of Fractional CO2 Laser Combined with Topical Type A Botulinum Toxin for Facial Rejuvenation: A Randomized Controlled Split-Face Study, BioMed Research International, 7 pages (2016).
International Search Report for PCT/US2019/060131 (Systems and Methods for Skin Treatment, filed Nov. 6, 2019) received from ISA/EP, 5 pages (dated Mar. 27, 2020).
Written Opinion for PCT/US2019/060131 (Systems and Methods for Skin Treatment, filed Nov. 6, 2019) received from ISA/EP, 7 pages (dated Mar. 27, 2020).

* cited by examiner

Strings of fat

1. Form hole in the skin and aspirate cored tissue through needle

2. Introduce wire in needle and rotate wire along needle axis

3. Remove wire and needle

METHODS AND DEVICES FOR MANIPULATING SUBDERMAL FAT

BACKGROUND OF THE INVENTION

Procedures and devices for removing fatty tissue, e.g., for cosmetic reasons, are common and represent a significant market in the cosmetic procedures sector. Conventional fat-removal procedures and devices, e.g., liposuction, can be disruptive to surrounding tissue and often include many risks such as excessive bleeding. There are relatively few procedures for removal of small amounts of fatty tissue, e.g., subcutaneous fat, for cosmetic purposes, and such procedures generally require a skilled practitioner for effective removal and can be very time-consuming and subject to complications. Accordingly, there is a need to provide a simple and safe method and apparatus for removal of subcutaneous fatty tissue.

SUMMARY OF THE INVENTION

In one aspect, the invention features a method of manipulating subdermal fat in a treatment area by a. inserting a first needle (e.g., a micro-coring needle) into the dermis of the treatment area followed by b. removing the needle from the treatment area. In this embodiment of the invention, the first needle includes a hollow tip and an elongated hollow shaft, the hollow tip being inserted to a depth that results in contact between the hollow tip and the subdermal fat, and the removal of the first needle resulting in the excision of dermis and/or subdermal fat from the treatment area.

The above methods can optionally further include inserting a second needle into the dermis proximate to the first needle (e.g., less than 5 cm, 1 cm, 5 mm, 4 mm, 3 mm, 2 mm, 1 mm, 0.5 mm, 0.1 mm or 0.05 mm from the first needle). These methods can also, e.g., include injecting a liquid (e.g., saline solution) into the treatment area via the second needle at a pressure sufficient to force fat through the first needle.

The above methods can further include the application of a suction force to the first and/or second needle while the tip is in contact with the subdermal fat. Here, the suction force results in subdermal fat being drawn into the needle. Alternatively, or additionally, a suction force is applied to the treatment area after the removal of the first and/or second needle. Here, the suction force results in subdermal fat being extruded from the treatment area.

In any of the foregoing embodiments, the method can further include mobilizing the subdermal fat in the treatment area prior to, during, or after insertion of a needle. This mobilization can include, e.g., introduction of a chemical agent (e.g., a detergent) that denatures fat cells in the subdermal fat (e.g., through the first and/or second needle), application of ultrasound, heating, cooling, or repeated cycles of heating or cooling of the subdermal fat (e.g., heating or cooling the first and/or second needle and/or applying or removing heat from outside the dermis, e.g., the in immediate proximity to the first and/or second needle), mechanically manipulating the subdermal fat (e.g., applying pressure from outside the dermis or directly contacting the subdermal fat with a disruption tool), and/or the application of tumescent anesthesia.

In some embodiments, the invention features repeating steps a. and b. at locations throughout the treatment area (e.g., between 5 and 100 locations per square centimeter of the treatment area). In any of the foregoing embodiments, the first and/or second needle can be, e.g., between 16 and 32 gauge (e.g., 17, 18, 19, 20, 21, 22, 23, 24, 25, 26, 27, 28, 29, 30, 31, or 32 gauge) and the areal fraction of skin removed can be, e.g., between 5% and 80%. The treatment area can be, e.g., between 1 cm$^2$ and 50 cm$^2$.

In certain embodiments, the treatment area includes cellulite. In embodiments where the treatment area is, e.g., cellulite, the methods of the invention can, e.g., further include severing septae in the subdermal fat of the treatment area. This severing can be accomplished, e.g., by i) deploying a wire including a bend into and through the first and/or second needle such that the bend exits from the tip; and ii) rotating the wire such that the end of the wire which has exited the tip contacts and severs the septae. In this embodiment, the wire is deployed while the needle tip is in contact with the subdermal fat. A suction force can optionally be applied to the first and/or second needle after the insertion but prior to the deploying of the wire.

In any foregoing aspects of the invention, the first and/or second needle can optionally include a smooth hollow lumen free of protuberances or barbs.

By "excised" tissue portion or "excision" is meant a removed tissue, including a tissue portion from a skin region, or the act of removing tissue or one or more tissue portions from a skin region. For example, an excision includes any removed tissue or tissue portion from a skin region, which can result in excised tissue portions having a particular geometry (e.g., a cylindrical geometry) and produce one or more holes (i.e., negative space created by the removal of tissue) in the skin region. Exemplary methods of forming excised tissue portions or excisions include use of one or more hollow needles (optionally include one or more notches, extensions, protrusions, and/or barbs), one or more microaugers, one or more microabraders, any useful tool for forming excisions, or any methods and apparatuses described herein.

By "subject" is meant a human or non-human animal (e.g., a mammal).

Other features and advantages of the invention will be apparent from the following Detailed Description and the claims.

DETAILED DESCRIPTION

In general, the present invention features methods of manipulating subdermal fat in a treatment area. Such methods include inserting a needle (e.g., a micro-coring needle) through the dermis to the subdermal fat layer in order to excise a portion of tissue from the treatment area. These insertions result in a portion of the dermis and a portion of subdermal fat to enter into the needle and/or enter the hole in the skin created by insertion of a needle. Removal of the needle results in excision of the portion of dermis and subdermal fat that entered into the needle. Additional subdermal fat can optionally be removed after removal of the needle via the hole left in the dermis by the tissue extraction. Additionally, or alternatively, subdermal fat can be removed by applying a suction force to the needle while inserted into the skin, resulting in additional subdermal fat being drawn into and though the needle or by applying a suction force to the skin after the needle has been removed, resulting in additional subdermal fat being extruded from the treated area. Additionally, fat may passively extrude through the openings created in the skin. Pressure may be applied to the fat layer to facilitate extrusion.

Further, the above methods may be supplemented by mobilization of the subdermal fat prior to, during, or after needle insertion. Such mobilization results in an increased propensity for subdermal fat to flow into the needle or flow through the holes left by the excision of a portion of dermis. For example, mechanical disruption of the fat layer may occur by movement of the penetrating member which may further facilitate extraction or extrusion.

In certain applications, the methods of the invention can be used to treat cellulite. Such treatments can, e.g., include the fat manipulation methods described above. Such treatments can further include severing of septae located with the affected tissue.

Embodiments of the invention are described in more detail below.

Methods of Subdermal Fat Mobilization

In certain embodiments of the invention, the subdermal fat in the treatment area is mobilized prior to, during, and/or after insertion of the needle. Methods of subdermal fat mobilization include liquefaction/degeneration of adipose tissue located in the treatment area, resulting in increased fat extraction through the micro-cored holes in the skin. The adipose tissue can, for example, be liquefied by:

Chemical modification: A chemical agent (e.g., a detergent) can be injected that denatures fat or the fat cells. The chemical agent can also be, e.g., a drug or compound that kills or otherwise disrupts fat cells. The agent can be injected prior to and/or after the treatment (e.g., along with the tumescent anesthesia solution) or during the treatment, using the needle (e.g., a micro-coring needle) after removal of the skin tissue contained in the needle. Alternatively, or additionally, a second needle can be inserted, e.g., in close proximity the first needle. The second needle can be, e.g., within 5 cm (e.g., within 1 cm, 5 mm, 4 mm, 3 mm, 2 mm, 1 mm, or 0.5 mm) of the first needle.

Mechanical modification: Disruption of fat tissue can be accomplished using ultrasonic energy (e.g., high-intensity focused ultrasound) prior to, during, or after the insertion of a needle. Alternatively, the treatment device can be modified by inserting a wire in the needle (e.g., micro-coring needle) or in a second needle located, e.g., in close proximity the first needle, while the needle tip is still positioned in the fat layer. The second needle can be, e.g., within 5 cm (e.g., within 1 cm, 5 mm, 4 mm, 3 mm, 2 mm, 1 mm, or 0.5 mm) from the first needle. The wire movement (e.g., rotation or vibration) can mechanically disrupt adipose tissue.

Thermal modification: Denaturation of the adipose tissue can be accomplished by application of heat or cold. The thermal modification can be applied by needles (e.g., by the micro-coring needles or secondary needles described above) inserted in the tissue (e.g. by heating or cooling the needles) or by another device prior to or during the treatment (e.g. laser, radio-frequency source). Furthermore, when fat mobilization is no longer desired, thermal modification (e.g., cooling) can be applied to slow or halt fat mobilization.

In cases where a second needle is used to aid in subdermal fat mobilization, the second needle can be either hollow or occluded.

Methods for Manipulation of Subdermal Fat

The present invention relates to methods of manipulating subdermal fat in a treatment area. These methods include excision of tissue portions (e.g., dermis and subdermal fat) using a needle (e.g., a micro-coring needle).

Such methods can include any part of the body, including the face (e.g., eyelid, cheeks, chin, forehead, lips, or nose), neck, chest (e.g., as in a breast lift), arms, legs, stomach, hips, buttocks, and/or back. Accordingly, the devices on the invention can be arranged or configured to be amenable to the size or geometry of different body regions. Such arrangements and configurations can include any useful shape (e.g., linear, curved, or stellate), size, and/or depth.

In one exemplary method, a plurality of tissue portions are excised from a treatment area of the skin (e.g., 1 cm$^2$, 5 cm$^2$, 10 cm$^2$, 20 cm$^2$, 30 cm$^2$, or 50 cm$^2$) in a subject (e.g., about 2, 3, 4, 5, 6, 7, 8, 9, 10, 15, 20, 25, 30, 35, 40, 45, 50, 75, 100, or more tissue portions, such as between about 2 and 100 tissue portions (e.g., between 2 and 10, 2 and 15, 2 and 20, 2 and 25, 2 and 30, 2 and 35, 2 and 40, 2 and 45, 2 and 50, 2 and 75, 5 and 10, 5 and 15, 5 and 20, 5 and 25, 5 and 30, 5 and 35, 5 and 40, 5 and 45, 5 and 50, 5 and 75, 5 and 100, 10 and 20, 10 and 25, 10 and 30, 10 and 35, 10 and 40, 10 and 45, 10 and 50, 10 and 75, 10 and 100, 15 and 20, 15 and 25, 15 and 30, 15 and 35, 15 and 40, 15 and 45, 15 and 50, 15 and 75, 15 and 100, 20 and 25, 20 and 30, 20 and 35, 20 and 40, 20 and 45, 20 and 50, 20 and 75, 20 and 100, 25 and 30, 25 and 35, 25 and 40, 25 and 45, 25 and 50, 25 and 75, 25 and 100, 30 and 35, 30 and 40, 30 and 45, 30 and 50, 30 and 75, 30 and 100, 35 and 40, 35 and 45, 35 and 50, 35 and 75, 35 and 100, 40 and 45, 40 and 50, 40 and 75, 40 and 100, 50 and 75, or 50 and 100)). Such tissue portions can be included in any useful geometric, non-geometric, or random array (e.g., such as those described herein for an array of needles). Such tissue portions can have any useful dimension that promotes wound or skin healing. Non-limiting dimensions of a tissue portion includes at least one dimension that is less than about 2.0 mm (e.g., less than or equal to about 1.5 mm, 1 mm, 0.75 mm, 0.5 mm, 0.3 mm, 0.2 mm, 0.1 mm, 0.075 mm, 0.05 mm, or 0.025 mm) or between about 0.025 mm and 2.0 mm (e.g., between about 0.025 mm and 1.5 mm, 0.025 mm and 1.0 mm, 0.025 mm and 0.75 mm, 0.025 mm and 0.5 mm, 0.025 mm and 0.3 mm, 0.025 mm and 0.2 mm, 0.025 mm and 0.1 mm, 0.025 mm and 0.075 mm, 0.025 mm and 0.05 mm, 0.05 mm and 2.0 mm, 0.05 mm and 1.5 mm, 0.05 mm and 1.0 mm, 0.05 mm and 0.75 mm, 0.05 mm and 0.5 mm, 0.05 mm and 0.3 mm, 0.05 mm and 0.2 mm, 0.05 mm and 0.1 mm, 0.05 mm and 0.075 mm, 0.075 mm and 2.0 mm, 0.075 mm and 1.5 mm, 0.075 mm and 1.0 mm, 0.075 mm and 0.75 mm, 0.075 mm and 0.5 mm, 0.075 mm and 0.3 mm, 0.075 mm and 0.2 mm, 0.075 mm and 0.1 mm, 0.1 mm and 2.0 mm, 0.1 mm and 1.5 mm, 0.1 mm and 1.0 mm, 0.1 mm and 0.75 mm, 0.1 mm and 0.5 mm, 0.1 mm and 0.3 mm, 0.1 mm and 0.2 mm, 0.2 mm and 2.0 mm, 0.2 mm and 1.5 mm, 0.2 mm and 1.0 mm, 0.2 mm and 0.75 mm, 0.2 mm and 0.5 mm, 0.2 mm and 0.3 mm, 0.3 mm and 2.0 mm, 0.3 mm and 1.5 mm, 0.3 mm and 1.0 mm, 0.3 mm and 0.75 mm, 0.3 mm and 0.5 mm, 0.5 mm and 2.0 mm, 0.5 mm and 1.5 mm, 0.5 mm and 1.0 mm, 0.5 mm and 0.75 mm, 0.75 mm and 2.0 mm, 0.75 mm and 1.5 mm, or 0.75 mm and 1.0 mm).

In some embodiments, the excised tissue portions forms a hole in the skin region, where the diameter or width of the hole is less than about 1.0 mm and results in a tissue portion having a diameter or width that is less than about 1.0 mm. In further embodiments, the tissue portion has a diameter or width that is less than about 1.0 mm and a length of more than about 1.0 mm (e.g., about 1.0 mm, 1.5 mm, 2.0 mm. 2.5 mm, 3.0 mm, or 3.5 mm). In particular embodiments, relatively small dimensions of the tissue portions can promote healing while minimizing the formation of scars.

In other embodiments, the excised tissue portions forms a slit in the skin region, where the length or width of the slit is less than about 1.0 mm and results in a tissue portion having a length or width that is less than about 1.0 mm. In further embodiments, the tissue portion has a length or width that is less than about 1.0 mm and a length of more than about 1.0 mm (e.g., about 1.0 mm, 1.5 mm, 2.0 mm. 2.5 mm, 3.0 mm, or 3.5 mm). In particular embodiments, relatively small dimensions of the tissue portions can promote healing while minimizing the formation of scars.

The tissue portion can be of any useful shape. Exemplary shapes include cylinders (i.e., thereby forming round or elongated holes in the skin region), holes (e.g., microholes), slits (e.g., microslits), elongated strips (i.e., thereby forming elongated openings in the skin region), or other geometries including at least dimension that is less than about 1.0 mm (e.g., less than or equal to about 0.75 mm, about 0.5 mm, about 0.3 mm, about 0.2 mm, about 0.1 mm, or about 0.05 mm) or between about 0.05 mm and 1.0 mm (e.g., 0.05 mm and 0.75 mm, 0.05 mm and 0.5 mm, 0.05 mm and 0.3 mm, 0.05 mm and 0.2 mm, 0.05 mm and 0.1 mm, 0.1 mm and 1.0 mm, 0.1 mm and 0.75 mm, 0.1 mm and 0.5 mm, 0.1 mm and 0.3 mm, 0.1 mm and 0.2 mm, 0.2 mm and 1.0 mm, 0.2 mm and 0.75 mm, 0.2 mm and 0.5 mm, 0.2 mm and 0.3 mm, 0.3 mm and 1.0 mm, 0.3 mm and 0.75 mm, 0.3 mm and 0.5 mm, 0.4 mm and 1.0 mm, 0.4 mm and 0.75 mm, 0.4 mm and 0.5 mm, 0.5 mm and 1.0 mm, 0.5 mm and 0.75 mm, 0.6 mm and 1.0 mm, 0.6 mm and 0.75 mm, or 0.75 mm and 1.0 mm). In other embodiments, the excised tissue portion has an areal dimension (e.g., a cross-sectional dimension in the xy-plane, such as an areal dimension of a circle or non-circular (e.g., elliptical) shape) of less than about or equal to about 1.0 $mm^2$ (e.g., less than or equal to about 0.9 $mm^2$, 0.8 $mm^2$, 0.7 $mm^2$, 0.6 $mm^2$, 0.5 $mm^2$, 0.4 $mm^2$, 0.3 $mm^2$, 0.2 $mm^2$, 0.1 $mm^2$, 0.07 $mm^2$, 0.05 $mm^2$, 0.03 $mm^2$, 0.02 $mm^2$, 0.01 $mm^2$, 0.007 $mm^2$, 0.005 $mm^2$, 0.003 $mm^2$, 0.002 $mm^2$, or 0.001 $mm^2$) or between about 0.001 $mm^2$ and 1.0 $mm^2$ (e.g., 0.001 $mm^2$ and 0.9 $mm^2$, 0.001 $mm^2$ and 0.8 $mm^2$, 0.001 $mm^2$ and 0.7 $mm^2$, 0.001 $mm^2$ and 0.6 $mm^2$, 0.001 $mm^2$ and 0.5 $mm^2$, 0.001 $mm^2$ and 0.4 $mm^2$, 0.001 $mm^2$ and 0.3 $mm^2$, 0.001 $mm^2$ and 0.2 $mm^2$, 0.001 $mm^2$ and 0.1 $mm^2$, 0.001 $mm^2$ and 0.07 $mm^2$, 0.001 $mm^2$ and 0.05 $mm^2$, 0.001 $mm^2$ and 0.03 $mm^2$, 0.001 $mm^2$ and 0.02 $mm^2$, 0.001 $mm^2$ and 0.01 $mm^2$, 0.001 $mm^2$ and 0.007 $mm^2$, 0.001 $mm^2$ and 0.005 $mm^2$, 0.001 $mm^2$ and 0.003 $mm^2$, 0.001 $mm^2$ and 0.002 $mm^2$, 0.002 $mm^2$ and 1.0 $mm^2$, 0.002 $mm^2$ and 0.9 $mm^2$, 0.002 $mm^2$ and 0.8 $mm^2$, 0.002 $mm^2$ and 0.7 $mm^2$, 0.002 $mm^2$ and 0.6 $mm^2$, 0.002 $mm^2$ and 0.5 $mm^2$, 0.002 $mm^2$ and 0.4 $mm^2$, 0.002 $mm^2$ and 0.3 $mm^2$, 0.002 $mm^2$ and 0.2 $mm^2$, 0.002 $mm^2$ and 0.1 $mm^2$, 0.002 $mm^2$ and 0.07 $mm^2$, 0.002 $mm^2$ and 0.05 $mm^2$ and 0.03 $mm^2$, 0.002 $mm^2$ and 0.02 $mm^2$, 0.002 $mm^2$ and 0.01 $mm^2$, 0.002 $mm^2$ and 0.007 $mm^2$, 0.002 $mm^2$ and 0.005 $mm^2$, 0.002 $mm^2$ and 0.003 $mm^2$, 0.005 $mm^2$ and 1.0 $mm^2$, 0.005 $mm^2$ and 0.9 $mm^2$, 0.005 $mm^2$ and 0.8 $mm^2$, 0.005 $mm^2$ and 0.7 $mm^2$, 0.005 $mm^2$ and 0.6 $mm^2$, 0.005 $mm^2$ and 0.5 $mm^2$, 0.005 $mm^2$ and 0.4 $mm^2$, 0.005 $mm^2$ and 0.3 $mm^2$, 0.005 $mm^2$ and 0.2 $mm^2$, 0.005 $mm^2$ and 0.1 $mm^2$, 0.005 $mm^2$ and 0.07 $mm^2$, 0.005 $mm^2$ and 0.05 $mm^2$, 0.005 $mm^2$ and 0.03 $mm^2$, 0.005 $mm^2$ and 0.02 $mm^2$, 0.005 $mm^2$ and 0.01 $mm^2$, 0.005 $mm^2$ and 0.007 $mm^2$, 0.007 $mm^2$ and 1.0 $mm^2$, 0.007 $mm^2$ and 0.9 $mm^2$, 0.007 $mm^2$ and 0.8 $mm^2$, 0.007 $mm^2$ and 0.7 $mm^2$, 0.007 $mm^2$ and 0.6 $mm^2$, 0.007 $mm^2$ and 0.5 $mm^2$, 0.007 $mm^2$ and 0.4 $mm^2$, 0.007 $mm^2$ and 0.3 $mm^2$, 0.007 $mm^2$ and 0.2 $mm^2$, 0.007 $mm^2$ and 0.1 $mm^2$, 0.007 $mm^2$ and 0.07 $mm^2$, 0.007 $mm^2$ and 0.05 $mm^2$, 0.007 $mm^2$ and 0.03 $mm^2$, 0.007 $mm^2$ and 0.02 $mm^2$, 0.007 $mm^2$ and 0.01 $mm^2$, 0.01 $mm^2$ and 1.0 $mm^2$, 0.01 $mm^2$ and 0.9 $mm^2$, 0.01 $mm^2$ and 0.8 $mm^2$, 0.01 $mm^2$ and 0.7 $mm^2$, 0.01 $mm^2$ and 0.6 $mm^2$, 0.01 $mm^2$ and 0.5 $mm^2$, 0.01 $mm^2$ and 0.4 $mm^2$, 0.01 $mm^2$ and 0.3 $mm^2$, 0.01 $mm^2$ and 0.2 $mm^2$, 0.01 $mm^2$ and 0.1 $mm^2$, 0.01 $mm^2$ and 0.07 $mm^2$, 0.01 $mm^2$ and 0.05 $mm^2$, 0.01 $mm^2$ and 0.03 $mm^2$, 0.01 $mm^2$ and 0.02 $mm^2$, 0.03 $mm^2$ and 1.0 $mm^2$, 0.03 $mm^2$ and 0.9 $mm^2$, 0.03 $mm^2$ and 0.8 $mm^2$, 0.03 $mm^2$ and 0.7 $mm^2$, 0.03 $mm^2$ and 0.6 $mm^2$, 0.03 $mm^2$ and 0.5 $mm^2$, 0.03 $mm^2$ and 0.4 $mm^2$, 0.03 $mm^2$ and 0.3 $mm^2$, 0.03 $mm^2$ and 0.2 $mm^2$, 0.03 $mm^2$ and 0.1 $mm^2$, 0.03 $mm^2$ and 0.07 $mm^2$, 0.03 $mm^2$ and 0.05 $mm^2$, 0.07 $mm^2$ and 1.0 $mm^2$, 0.07 $mm^2$ and 0.9 $mm^2$, 0.07 $mm^2$ and 0.8 $mm^2$, 0.07 $mm^2$ and 0.7 $mm^2$, 0.07 $mm^2$ and 0.6 $mm^2$, 0.07 $mm^2$ and 0.5 $mm^2$, 0.07 $mm^2$ and 0.4 $mm^2$, 0.07 $mm^2$ and 0.3 $mm^2$, 0.07 $mm^2$ and 0.2 $mm^2$, 0.07 $mm^2$ and 0.1 $mm^2$, 0.1 $mm^2$ and 1.0 $mm^2$, 0.1 $mm^2$ and 0.9 $mm^2$, 0.1 $mm^2$ and 0.8 $mm^2$, 0.1 $mm^2$ and 0.7 $mm^2$, 0.1 $mm^2$ and 0.6 $mm^2$, 0.1 $mm^2$ and 0.5 $mm^2$, 0.1 $mm^2$ and 0.4 $mm^2$, 0.1 $mm^2$ and 0.3 $mm^2$, 0.1 $mm^2$ and 0.2 $mm^2$, 0.3 $mm^2$ and 1.0 $mm^2$, 0.3 $mm^2$ and 0.9 $mm^2$, 0.3 $mm^2$ and 0.8 $mm^2$, 0.3 $mm^2$ and 0.7 $mm^2$, 0.3 $mm^2$ and 0.6 $mm^2$, 0.3 $mm^2$ and 0.5 $mm^2$, 0.3 $mm^2$ and 0.4 $mm^2$, 0.5 $mm^2$ and 1.0 $mm^2$, 0.5 $mm^2$ and 0.9 $mm^2$, 0.5 $mm^2$ and 0.8 $mm^2$, 0.5 $mm^2$ and 0.7 $mm^2$, 0.5 $mm^2$ and 0.6 $mm^2$, 0.7 $mm^2$ and 1.0 $mm^2$, 0.7 $mm^2$ and 0.9 $mm^2$, or 0.7 $mm^2$ and 0.8 $mm^2$). When viewed from the top of the skin, the shape of the hole can be circular or non-circular (e.g., elliptical). Exemplary shapes of tissue portions are provided in FIGS. 1A-1C and 3A-3C and its associated text of U.S. Pub. No. 2012/0041430, which are hereby incorporated by reference in its entirety Any beneficial areal fraction of the skin region can be removed, such as an areal fraction of less than about 70% (e.g., less than about 65%, 60%, 55%, 50%, 45%, 40%, 35%, 30%, 25%, 20%, 10%, or 5%) or such as between about 5% and 80% (e.g., between about 5% and 10%, 5% and 10%, 5% and 20%, 5% and 25%, 5% and 30%, 5% and 35%, 5% and 40%, 5% and 45%, 5% and 50%, 5% and 55%, 5% and 60%, 5% and 65%, 5% and 70%, 5% and 75%, 10% and 10%, 10% and 20%, 10% and 25%, 10% and 30%, 10% and 35%, 10% and 40%, 10% and 45%, 10% and 50%, 10% and 55%, 10% and 60%, 10% and 65%, 10% and 70%, 10% and 75%, 10% and 80%, 15% and 20%, 15% and 25%, 15% and 30%, 15% and 35%, 15% and 40%, 15% and 45%, 15% and 50%, 15% and 55%, 15% and 60%, 15% and 65%, 15% and 70%, 15% and 75%, 15% and 80%, 20% and 25%, 20% and 30%, 20% and 35%, 20% and 40%, 20% and 45%, 20% and 50%, 20% and 55%, 20% and 60%, 20% and 65%, 20% and 70%, 20% and 75%, or 20% and 80%).

Furthermore, the plurality of tissue portions can be excised in any beneficial pattern within the skin region.

Exemplary patterns within the skin region include tile patterns or fractal-like shapes, where the array of hollow tubes can be arranged, e.g., in a base, to effectuate such a pattern. For example, a higher density and/or smaller spacing of tissue portions (e.g., slits and/or holes) can be excised in the skin in center of the pattern or in thicker portions of the skin. In another example, the pattern within the skin can be random, staggered rows, parallel rows, a circular pattern, a spiral pattern, a square or rectangular pattern, a triangular pattern, a hexagonal pattern, a radial distribution, or a combination of one or more such patterns of the incised or excised tissue portions. The pattern can arise from modifications to the average length, depth, or width of an incised or excised tissue portion, as well as the density, orientation, and spacing between such incisions and/or excisions (e.g., by using an apparatus having one or more needles with differing lengths, widths, or geometries that are arranged in a particular density or spacing pattern). Such patterns can be optimized to promote unidirectional, non-directional, or multidirectional contraction or expansion of skin (e.g., in the x-direction, y-direction, x-direction, x-y plane, y-z plane, x-z plane, and/or xyz-plane), such as by modifying the average length, depth, width, density, orientation, and/or spacing between incisions and/or excisions.

In addition to subdermal fat, any useful portion of the skin can be excised. Such tissue portions can include epidermal tissue, dermal tissue, and/or cells or tissue proximal to the dermal/fatty layer boundary (e.g., stem cells). In particular embodiments, the excised tissue portions forms a hole in the skin region, where the depth of the hole is more than about 1.0 mm and results in a tissue portion having a length that is more than about 1.0 mm (e.g., about 1.0 mm, 1.5 mm, 2.0 mm. 2.5 mm, 3.0 mm, or 3.5 mm). The holes can, e.g., extend up to, or into the subdermal fat region. In particular embodiments, the incised or excised tissue portions forms a slit in the skin region, where the depth of the slit is more than about 1.0 mm and results in a tissue portion having a length that is more than about 1.0 mm (e.g., about 1.0 mm, 1.5 mm, 2.0 mm. 2.5 mm, 3.0 mm, or 3.5 mm). The slits can, e.g., extend up to, or into the subdermal fat region. In some embodiments, the tissue portion has a length that corresponds to a typical total depth of the skin layer (e.g., epidermal and dermal layers). Based on the part of the body, the total depth of the epidermal and dermal layers can vary. In some embodiments, the depth of the epidermal layer is between about 0.8 mm to 1.4 mm, and/or the depth of the dermal layer is between about 0.3 mm to 4.0 mm. In other embodiments, the total depth of the skin layer (e.g., epidermal and dermal layers) is between about 1.0 mm and 5.5 mm, thereby resulting in a tissue portion having a length between about 1.0 mm and 5.5 mm (e.g., between about 1.0 mm and 1.5 mm, 1.0 mm and 2.0 mm, 1.0 mm and 2.5 mm, 1.0 mm and 3.0 mm, 1.0 mm and 3.5 mm, 1.0 mm and 4.0 mm, 1.0 mm and 4.5 mm, 1.0 mm and 5.0 mm, 1.5 mm and 2.0 mm, 1.5 mm and 2.5 mm, 1.5 mm and 3.0 mm, 1.5 mm and 3.5 mm, 1.5 mm and 4.0 mm, 1.5 mm and 4.5 mm, 1.5 mm and 5.0 mm, 1.5 mm and 5.5 mm, 2.0 mm and 2.5 mm, 2.0 mm and 3.0 mm, 2.0 mm and 3.5 mm, 2.0 mm and 4.0 mm, 2.0 mm and 4.5 mm, 2.0 mm and 5.0 mm, 2.0 and 5.5 mm, 2.5 mm and 3.0 mm, 2.5 mm and 3.5 mm, 2.5 mm and 4.0 mm, 2.5 mm and 4.5 mm, 2.5 mm and 5.0 mm, 2.5 mm and 5.5 mm, 3.0 mm and 3.5 mm, 3.0 mm and 4.0 mm, 3.0 mm and 4.5 mm, 3.0 mm and 5.0 mm, 3.0 and 5.5 mm, 3.5 mm and 4.0 mm, 3.5 mm and 4.5 mm, 3.5 mm and 5.0 mm, 3.5 and 5.5 mm, 4.0 mm and 4.5 mm, 4.0 mm and 5.0 mm, 4.0 and 5.5 mm, 4.5 mm and 5.0 mm, 4.5 and 5.5 mm, or 5.0 mm and 5.5 mm). In yet other embodiments, the average total depth of the tissue portion or the skin layer (e.g., epidermal and dermal layers) is about 1.5 mm. In yet other embodiments, the average total depth of the tissue portion or the skin layer (e.g., epidermal and dermal layers) is about 3 mm.

Excisions can be performed by a micro-coring needle. For example, a plurality of excised tissue portions can be achieved by use of one or more micro-coring needles characterized as hollow tubes or needles (e.g., where the inner diameter of at least one tube is less than about 0.5 mm, about 0.3 mm, or about 0.2 mm) or one or more solid tubes or needles. Exemplary components for performing excisions include a needle (e.g., a 16 gauge needle having an inner diameter of 1.194 mm; an 18 gauge needle having an inner diameter of 0.838 mm; a 20 gauge needle having an inner diameter of 0.564 mm; a 23 gauge needle having an inner diameter of about 0.337 mm and an outer diameter of about 0.51 mm, thereby resulting in a tissue portion having a dimension (e.g., a width or diameter) of about 0.3 mm; a 25 gauge needle having an inner diameter of about 0.26 mm or a thin-walled 25 gauge needle having an inner diameter of about 0.31 mm and an outer diameter of about 0.51 mm, thereby resulting in a tissue portion having a dimension (e.g., a width or diameter) of about 0.2 mm; a 30 gauge needle having an inner diameter of about 0.159 mm; a 32 gauge needle having an inner diameter of about 0.108 mm; or a 34 gauge needle having an inner diameter of about 0.0826 mm).

The geometry of the one or more micro-coring needles can include at least two points (or prongs) (e.g., at least three, four, five, six, seven, eight, or more points) provided at a distal end of the tube (e.g., to facilitate separation of the tissue portions from the surrounding tissue and/or insertion of the tubes into the skin region), where an angle formed by at least one of the points is about thirty degrees. Exemplary micro-coring needles include those having two points (e.g., by grinding in orientations that are 180 degrees apart), three points (e.g., by grinding in orientations that are 120 degrees apart), or four points (e.g., by grinding in orientations that are 90 degrees apart). The points can optionally include a beveled edge (e.g., to further facilitate separation of tissue portions or insertion of tubes).

The points can have any useful geometric configuration. In one example, the micro-coring needle has a longitudinal axis (i.e., along the length of the needle) and a diameter (i.e., through the cross-section of the needle), as well as a proximal end and the distal end. The distal end can include one or more points, where each point is characterized by angle $\alpha$ (i.e., the angle between each of the opposing lateral sides of the tube that forms the point and the longitudinal axis of the tube). When viewed from the side, the angle formed by a point is characterized by angle $2\alpha$. For example, a tip angle of about 30 degrees corresponds to an angle $\alpha$ of about 15 degrees. Furthermore, the angled distal end of the tube can be formed (e.g., by grinding or cutting) at angle $\alpha$, e.g., to form a second bevel structure at the distal end of a tube, where this second bevel is characterized by angle $\beta$ and is orthogonal to the primary point (or bevel) characterized by angle $\alpha$. This second bevel can be provided to reduce the size or width of the point. Exemplary angle $\alpha$ and $\beta$ includes less than about 20 degrees, 15 degrees, 10, degrees, or 5 degrees (e.g., about 15 degrees, 10 degrees, 6 degrees, 5 degrees, or 3 degrees). See, e.g., FIGS. 8A-8J and its associated text of U.S. Pub. No. 2011/0313429, which are hereby incorporated by reference in its entirety, for exemplary points, angle $\alpha$, and angle $\beta$.

The micro-coring needles can optionally include one or more notches within the lumen of the needle and/or extensions on the exterior surface of the needle (e.g., at the distal portion of the needle). Such notches and extensions could be useful to promote cutting of tissue surrounding the excised tissue portions. Exemplary needles having such notches and/or extensions include a microauger, as well as any needles provided in FIGS. 5A-5E and described its associated text of International Pub. No. WO 2012/103492, which are hereby incorporated by reference in its entirety, for apparatuses having notches and/or extensions.

The micro-coring needles can optionally include one or more protrusions or barbs within the lumen of the needle to promote retention of fat within the needle. In use, an apparatus including such needles can be inserted into the subcutaneous fat layer and then withdrawn to remove retained fat tissue. See, e.g., FIGS. 1A-1C, 2A-2C, 3A, 4, 5A-5C, 6A-6B, 7, and 8A-8C and its associated text of International Pub. No. WO 2013/013196, which are hereby incorporated by reference in its entirety, for apparatuses having protrusions or barbs. In certain preferred embodiments, the micro-coring needles do not include protrusions or barbs within the lumen of the needle.

The components for making or excisions can be provided in any useful arrangement (e.g., a linear array, a radial array, or any described herein) of one or more components (e.g., two, three, four, five, ten, thirty, fifty, hundred, or more). The spacing between each component (e.g., needle) can be of any useful dimension, such as between about 1 mm and 50 mm (e.g., between about 1 mm and 40 mm, 1 mm and 30 mm, 1 mm and 25 mm, 1 mm and 20 mm, 1 mm and 15 mm, 1 mm and 10 mm, 1 mm and 5 mm, 1 mm and 3 mm, 3 mm and 50 mm, 3 mm and 40 mm, 3 mm and 30 mm, 3 mm and 25 mm, 3 mm and 20 mm, 3 mm and 15 mm, 3 mm and 10 mm, 3 mm and 5 mm, 5 mm and 50 mm, 5 mm and 40 mm, 5 mm and 30 mm, 5 mm and 25 mm, 5 mm and 20 mm, 5 mm and 15 mm, 5 mm and 10 mm, 10 mm and 50 mm, 10 mm and 40 mm, 10 mm and 30 mm, 10 mm and 25 mm, 10 mm and 20 mm, 10 mm and 15 mm, 15 mm and 50 mm, 15 mm and 40 mm, 15 mm and 30 mm, 15 mm and 25 mm, 15 mm and 20 mm, 20 mm and 50 mm, 20 mm and 40 mm, 20 mm and 30 mm, 20 mm and 25 mm, 30 mm and 50 mm, 30 mm and 40 mm, or 40 mm and 50 mm). Such arrangements can include one or more needles (e.g., about 2, 3, 4, 5, 6, 7, 8, 9, 10, 15, 20, 25, 30, 35, 40, 45, 50, 75, 100, or more needles, such as between about 2 and 100 needles (e.g., between 2 and 10, 2 and 15, 2 and 20, 2 and 25, 2 and 30, 2 and 35, 2 and 40, 2 and 45, 2 and 50, 2 and 75, 5 and 10, 5 and 15, 5 and 20, 5 and 25, 5 and 30, 5 and 35, 5 and 40, 5 and 45, 5 and 50, 5 and 75, 5 and 100, 10 and 20, 10 and 25, 10 and 30, 10 and 35, 10 and 40, 10 and 45, 10 and 50, 10 and 75, 10 and 100, 15 and 20, 15 and 25, 15 and 30, 15 and 35, 15 and 40, 15 and 45, 15 and 50, 15 and 75, 15 and 100, 20 and 25, 20 and 30, 20 and 35, 20 and 40, 20 and 45, 20 and 50, 20 and 75, 20 and 100, 25 and 30, 25 and 35, 25 and 40, 25 and 45, 25 and 50, 25 and 75, 25 and 100, 30 and 35, 30 and 40, 30 and 45, 30 and 50, 30 and 75, 30 and 100, 35 and 40, 35 and 45, 35 and 50, 35 and 75, 35 and 100, 40 and 45, 40 and 50, 40 and 75, 40 and 100, 50 and 75, or 50 and 100)).

Such arrangements of components can be any of various two-dimensional or three-dimensional patterns along a base holding one or more components for making excisions. The base can be optionally mounted on a roller apparatus having a cylindrical body with a longitudinal rotational axis, where the one or more needles are arranged on the longitudinal surface of the cylindrical body. In some embodiments, the needles extend as substantially coplanar extensions of the cylindrical body. In use, rotation of the cylindrical body along the skin results in the excision of tissue portions by the needles. Exemplary roller apparatuses are provided in FIGS. 11A-11B and its associated text in U.S. Pub. No. 2011/0251602, in FIGS. 3A-3B and its associated text in International Pub. No. WO 2012/103492, which are hereby incorporated by reference in its entirety.

Such components for making excisions can include one or more stop arrangements (e.g., one or more collars, which can be coupled to the outer portion of the needle and be adjusted along the long axis of the needle to control the depth of excision in the biological tissue); one or more sleeves around a portion of a needle, such that the sleeve is slidably translatable along the longitudinal axis of the needle (e.g., to excise tissue portions below the surface of the skin region); a vibrating arrangement (e.g., a piezoelectric element, a solenoid, a pneumatic element, ultrasonic element, or a hydraulic element) that mechanically couples to at least one needle (e.g., to promote insertion of one or more needles into the skin region, such as by providing an amplitude of vibration in the range of about 50-500 μm (e.g., between about 100-200 μm) or by providing a frequency of the induced vibrations to be between about 10 Hz and about 10 kHz (e.g., between about 500 Hz and about 2 kHz, or even about 1 kHz)); a suction or pressure system (e.g., by squeezing a flexible bulb or deformable membrane attached thereto or by opening a valve leading from a source of elevated pressure, such as a small pump) to stabilize the surrounding skin region prior to excision and/or to facilitate removal of the skin portions and/or subdermal fat from the tube; a pin within the lumen to the tube to facilitate removal of the skin portions or subdermal fat from the tube; one or more actuators for positioning, translating, and/or rotating the one or more needles relative to the skin portion or relative to the optional one or more pins; a housing or frame to stabilize the surrounding skin region prior to excision; one or more actuators for positioning and/or translating the one or more pins relative to the skin portion or relative to one or more needles; one or more sensors (e.g., force sensors, optical sensors, laser fibers, photodetectors, and/or position sensors) in communication with one or more needles to detect the position of the needles, the presence of a tissue portion in the needle, the position of the apparatus relative to the treated skin portion; a reciprocating arrangement attached to a base or a substrate having one or more attached needles (e.g., a motor or actuator configured to repeatedly insert and/or withdrawn one or more needles); a fluid system coupled to the needles to facilitate removal of excised tissue portions or to irrigate the skin portion, e.g., with saline or a phosphate buffered solution; a heat source (e.g., a resistive heater or current) in communication with the needle to promote cauterization or ablation of tissue portions or mobilization of fat in or around the needle; an optical element (e.g., a lens, a prism, a reflector, etc.) to facilitate viewing of the skin portion beneath the apparatus, needle; and/or an abrading element optionally mounted on a rotating shaft (e.g., to promote dermabrasion).

The needles can be formed from any useful material and optionally coated or chemically treated to promote excision of a tissue portion and subdermal fat and/or to increase precision or effectiveness for treating the skin region. Exemplary materials include metal (e.g., a stainless steel tube, 304 stainless steel, a surgical stainless steel), a biopsy needle, an epoxy, a glass, a polymer, a plastic, a resin, another structurally rigid material, or a similar structure. Exemplary coatings include a lubricant, a low-friction material (e.g., Teflon™), a chromium coating (e.g., ME-92™, such as to increase material strength), a plastic, a polymer (e.g., nylon or polyethylene), a polished metal alloy, or the like.

In particular embodiments, an apparatus for manipulating subdermal fat includes at least one needle including at least two points provided at a distal end thereof and an optional stop arrangement coupled to the outer portion of the tube (e.g., to control and/or limit a distance to which the one needle is inserted into a biological tissue), where the angle formed by at least one of the points is about thirty degrees, where the inner diameter of at least one needle is less than about 1 mm, and where at least one section of the needle is structured to be inserted into a biological tissue to excise at least one tissue therefrom when the tube is withdrawn from the tissue. In other embodiments, the apparatus further includes a pin provided at least partially within the central lumen of a needle, where the pin is controllably translatable in a direction along a longitudinal axis of the one needle and the pin is configured to facilitate removal of at least one tissue portion (e.g., subdermal fat) from the tube. In yet other embodiments, the apparatus includes a substrate; a plurality of needles affixed to the substrate and configured to be at least partially inserted into a biological tissue; at least one opening provided on or in a wall of each of the needles; at least one cutting edge protruding from the wall of each of the needles proximal to the at least one opening; and a sleeve provided around at least a portion of each of the needle, where each needle is configured to be translatable along a longitudinal axis of a corresponding sleeve, and where a distance from the longitudinal axis of each needle to an outer edge of each corresponding sleeve is at least as large as a distance from the longitudinal axis of the tube to an outer portion of the cutting edge of the tube.

The procedures herein can include one or more optional processes that promote effective excision of tissue portions or that benefit healing or mobilize subdermal fat. Such optional processes include cooling, freezing, or partially freezing the skin portion prior to skin excision (e.g., by applying a cryospray or by contacting a surface of a skin region with a cooled object for an appropriate duration), where such cooling and/or freezing can, e.g., increase mechanical stability of the tissue portions and/or mobilize subdermal fat; treatment with red or near-infrared light of the skin portion to further promote healing of the tissue; and/or treatment with an optical energy source, such as any described herein (e.g., an ablative laser).

Exemplary procedures, methods, and apparatuses are provided in U.S. Pub. Nos. 2012/0041430, 2011/0313429, 2011/0251602, 2012/0226214, 2012/0226306 and 2012/0226214; International Pub. Nos. WO 2012/103492, WO 2012/103483, WO 2012/103488, WO 2013/013199, WO 2013/013196, and WO 2012/119131; Fernandes et al., "Micro-Mechanical Fractional Skin Rejuvenation," *Plastic & Reconstructive Surgery* 130(5S-1):28 (2012); and Fernandes et al., "Micro-Mechanical Fractional Skin Rejuvenation," *Plastic & Reconstructive Surgery* 131(2):216-223 (2013), where each is hereby incorporated by reference in its entirety.

In certain embodiments, the methods of the invention include applying pressure to the treatment area to facilitate fat removal. In one embodiment, pressure can be applied to the treatment area prior to insertion of a needle, thereby facilitating fat entry into the needle once inserted. In another embodiment, pressure can be applied while the needle is inserted (e.g., by a second needle as described above), thereby causing subdermal fat to flow into and, in some cases, through the needle. Finally, certain embodiments feature applying pressure after the needle is removed, thereby causing subdermal fat to escape the dermis through the holes left by the excised tissue. Alternatively, a vacuum source may be applied to the external surface of the cored region to aid in fat extrusion. Heat and other mechanical stimuli may further facilitate fat extrusion.

EXAMPLES

Example 1

Subdermal Fat Modulation

Figure 1:
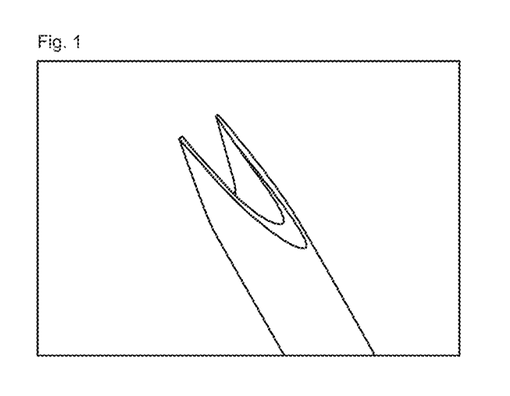
FIG. 1 is a photograph of a micro-coring needle.
Figure 2:
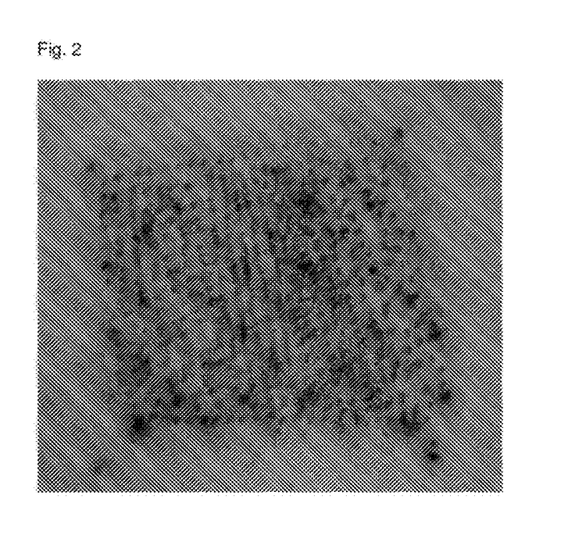
FIG. 2 is a photograph of an area of tissue treated with a micro-coring needle.
Figure 3:
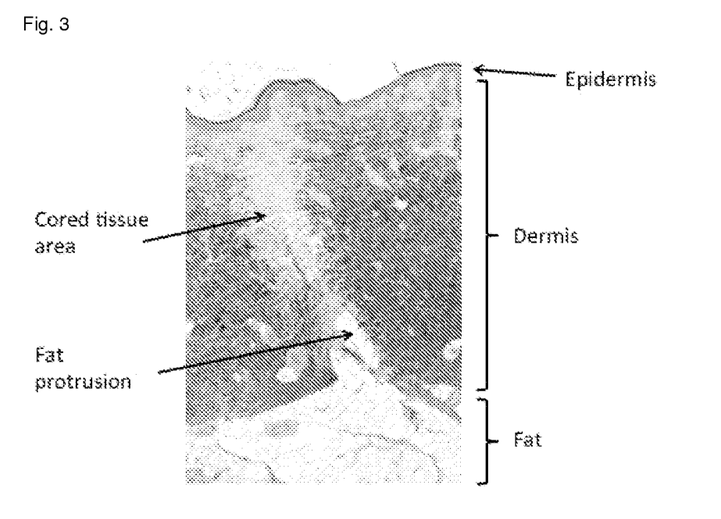
FIG. 3 is a photograph of a section of tissue showing cored tissue area.
Figure 4:
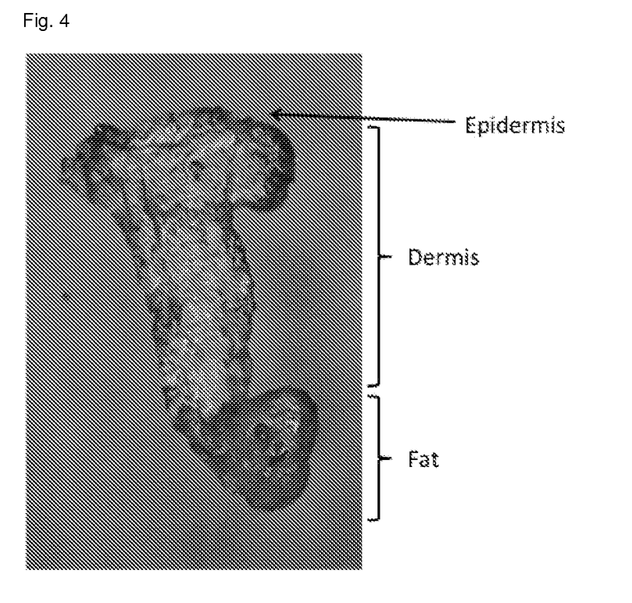
FIG. 4 is a photograph of a portion of tissue removed by a micro-coring needle.

Micro-coring needles allow excision of small columns of skin as described, e.g., in "Method and apparatus for dermatological treatment" from Anderson et al. (PCT Application Publication No. 2011/0313429, herein incorporated by reference). FIG. 1 shows an exemplary embodiment of a micro-coring needle. The needle is inserted in the skin until its tip protrudes in the subcutaneous fat layer allowing tissue excision. FIG. 2 shows a picture of a treated area. The treatment resulted in the formation of small holes though the skin. FIG. 3 shows a picture of a skin section treated with a micro-coring needle one week after treatment. It shows that, where a column of epidermal and dermal tissue was removed, the removed tissue is replaced by granulation tissue. Removal of the column of skin tissue generated herniation fat in the dermis. The removed column of skin (epidermis and dermis) is attached to fat cells as shown in FIG. 4. The sample was stained with Oil Red O, which preferentially stains fat. The sample includes skin tissue attached to adipose tissue.

Tumescent anesthesia is a local anesthesia technique requiring the infiltration of a large volume of fluid in the area to be treated. The injected fluid typically consists of lidocaine and epinephrine highly diluted in physiologic saline solution. Tumescent anesthesia prior to treatment with micro-coring needles can result in (1) local anesthesia of tissue, (2) reduction of bleeding during the treatment, (3) increased sub-cutaneous pressure, and (4) chemical modification of the sub-cutaneous fat.

Figure 5:
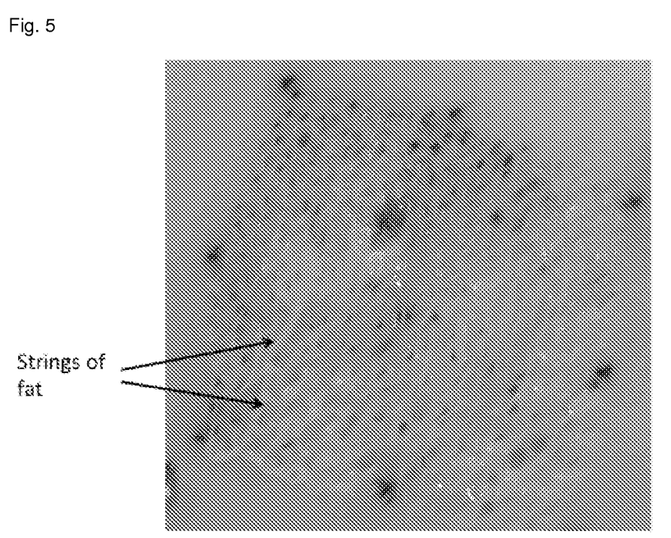
FIG. 5 is a photograph of subdermal fat extrusion in an area of tissue treated with a micro-coring needle.

FIG. 5 shows an area of skin treated with tumescent anesthesia prior to treatment with microcoring needles. As seen in this figure, prominent strings of fat emerge from the tissue treated with micro-coring needles.

Example 2

Cellulite Treatment

Figure 6:
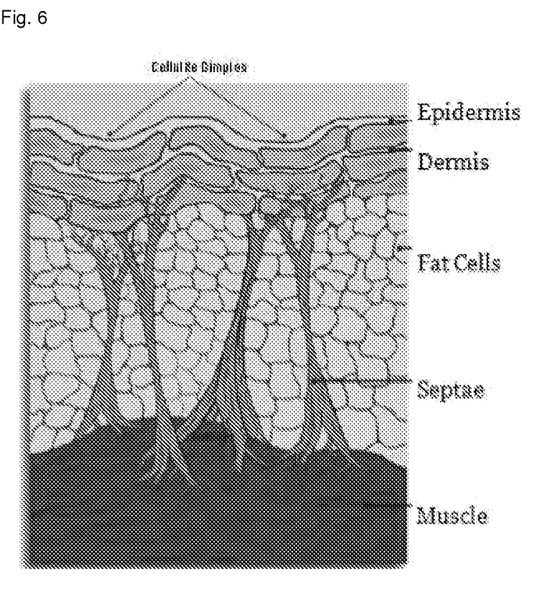
FIG. 6 is a schematic showing features of tissue characterized by cellulite.
Figure 7:
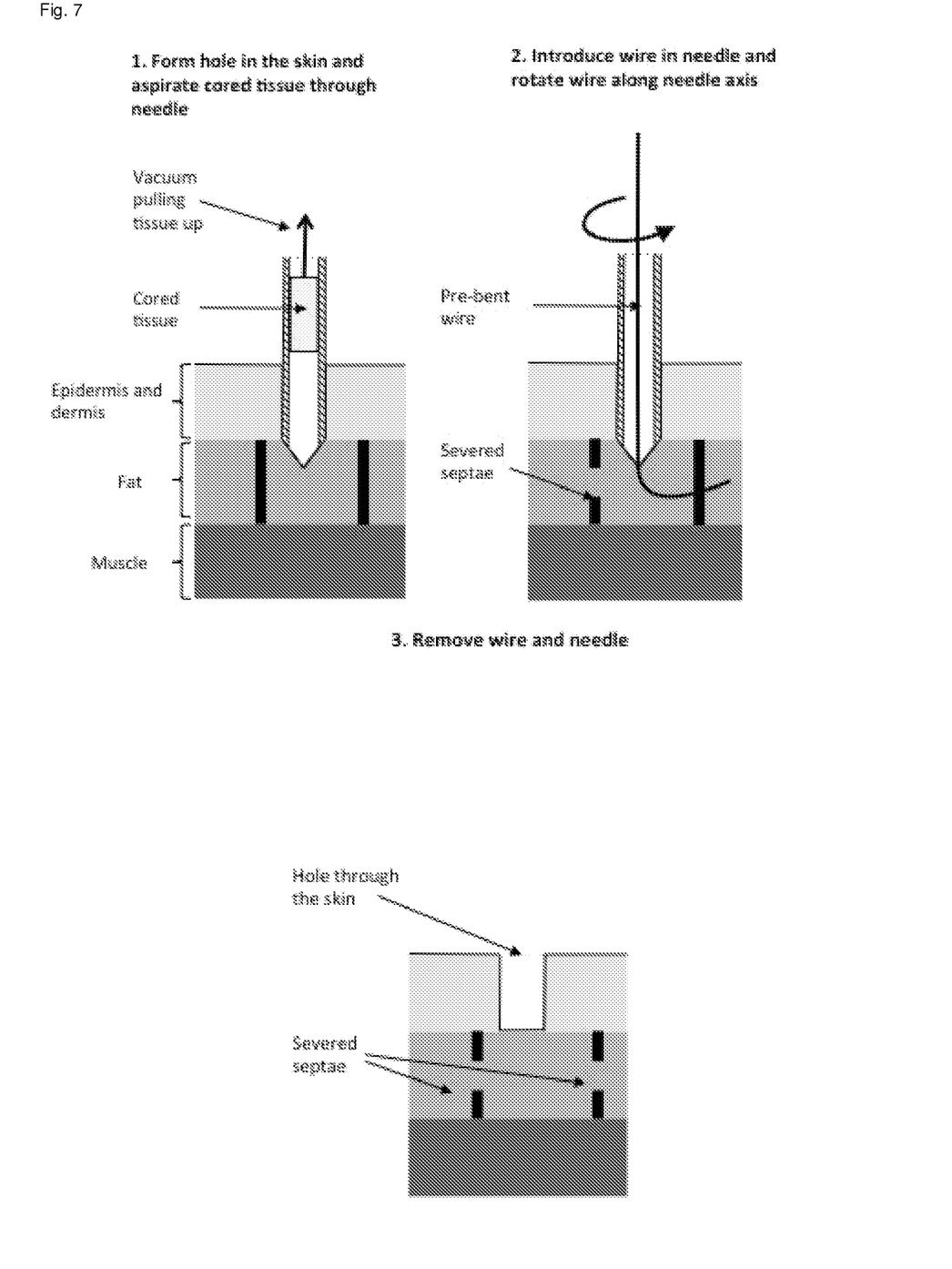
FIG. 7 is a series of schematics showing application of a needle modified to facilitate treatment of cellulite.

Cellulite is characterized by dimpling or nodularity of the skin. Cellulite is thought to be formed by herniation of subcutaneous fat into the dermis. Formation of fibrotic bands (septae) between the subcutaneous tissue and the dermis and weakening of the mechanical properties of the dermis (e.g. breakdown of collagen in reticular dermis) result in the formation of nodules or dimples as illustrated in FIG. 6.

Modified micro-coring needles (see, e.g., FIG. 7) allow severing of the septae. The needle is inserted into the skin until its tip protrudes in the fat layer. The cored skin is aspirated by applying a vacuum on the needle. A pre-bent wire is introduced in the needle while the needle tip is still in the subcutaneous layer. The pre-bent wire is deployed in the fat layer. It is then rotated around the needle axis as to sever septae surrounding the needle. The wire is the retracted and the needle is removed. The cellulite treatment described above: (1) severs the septae, (2) improves the mechanical properties of the skin, and (3) allows fat extraction through the hole in the skin.

Other Embodiments

All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, pharmacology, or related fields are intended to be within the scope of the invention.

The invention claimed is:

1. A method of manipulating subdermal fat in a treatment area, said method comprising:
   i. inserting a first microcoring needle into dermis of said treatment area followed by
   ii. removing said first microcoring needle from said treatment area,
   repeating steps i and ii throughout the treatment area, wherein an areal fraction of skin removed is between 5% and 10% of the treatment area, and
   wherein:
   said first microcoring needle is between 16 and 32 gauge and comprises a hollow tip and an elongated hollow shaft, said hollow tip is inserted to a depth that results in contact between said hollow tip and said subdermal fat, and said removal of said first microcoring needle results in the excision of dermis and/or subdermal fat from said treatment area, wherein said treatment area comprises cellulite,
   iii. severing septae in the subdermal fat of said treatment area by deploying a wire comprising a bend into and through said first microcoring needle such that said bend exits from said hollow tip; and rotating said wire such that the end of said wire which has exited said hollow tip contacts and severs said septae;
   wherein said wire is deployed while said hollow tip is in contact with said subdermal fat.

2. The method of claim 1, wherein said first microcoring needle is vibrated or rotated after insertion and prior to removal from said treatment area.

3. The method of claim 1, further comprising application of a suction force to said first microcoring needle while said hollow tip is in contact with said subdermal fat, wherein said suction force results in subdermal fat being drawn into said first microcoring needle.

4. The method of claim 1, wherein a suction force is applied to said treatment area after the removal of said first microcoring needle, wherein said suction force results in subdermal fat being extruded from said treatment area.

5. The method of claim 1, further comprising mobilizing said subdermal fat in said treatment area prior to said insertion of said first microcoring needle.

6. The method of claim 1, further comprising mobilizing said subdermal fat in said treatment area after said removal of said first microcoring needle from said treatment area.

7. The method of claim 1, further comprising mobilizing said subdermal fat in said treatment area while said first microcoring needle is inserted into said treatment area.

8. The method of claim 7, wherein said mobilizing of said subdermal fat comprises introduction of a chemical agent that denatures fat cells in said subdermal fat.

9. The method of claim 7, wherein said mobilizing of said subdermal fat comprises application of ultrasound.

10. The method of claim 7, wherein said mobilizing of said subdermal fat comprises heating, cooling, or repeated cycles of heating or cooling of said subdermal fat.

11. The method of claim 10, wherein said heating or cooling of said subdermal fat comprises heating or cooling said first microcoring needle and/or applying or removing heat from outside the dermis.

12. The method of claim 10, wherein said heating or cooling of said subdermal fat comprises heating or cooling said treatment area in the immediate proximity of the first microcoring needle.

13. The method of claim 7, wherein said mobilizing of said subdermal fat comprises mechanically manipulating said subdermal fat.

14. The method of claim 13, wherein said mechanical manipulation is selected from the group consisting of applying pressure from outside the dermis and directly contacting the subdermal fat with a disruption tool.

15. The method of claim 7, wherein said mobilizing of said subdermal fat comprises application of tumescent anesthesia.

16. The method of claim 1, where the treatment area is between 1 $cm^2$ and 50 $cm^2$.

17. The method of claim 1, wherein a suction force is applied to said first microcoring needle after said insertion but prior to said deploying of said wire.

18. The methods of claim 1, wherein said first microcoring needle comprises a smooth hollow lumen free of protuberances or barbs.

19. The methods of claim 1, wherein said method further comprises inserting a second microcoring needle into dermis proximate to said first microcoring needle.

20. The method of claim 19, wherein, when inserted, said second microcoring needle and said first microcoring needle are less than 1 cm, 5 mm, or 1 mm apart.

21. The method of claim 19, wherein said second microcoring needle is vibrated or rotated to mobilize said subdermal fat.

22. The method of claim 19, wherein a chemical agent is introduced into said second microcoring needle to disrupt said subdermal fat.

23. The method of claim 19, wherein a liquid is injected into said treatment area via said second microcoring needle at a pressure sufficient to force fat through said first microcoring needle.

24. The method of claim 23, wherein said liquid is a solution of saline in water.

* * * * *